(12) United States Patent
Niijima et al.

(10) Patent No.: US 8,058,444 B2
(45) Date of Patent: *Nov. 15, 2011

(54) HETEROCYCLE-SUBSTITUTED PYRIDINE DERIVATIVE'S SALT OR CRYSTAL THEREOF

(75) Inventors: Jun Niijima, Tsukuba (JP); Kazutaka Nakamoto, Tsukuba (JP); Masayuki Matsukura, Tsukuba (JP); Keigo Tanaka, Tsukuba (JP); Eiichi Yamamoto, Tsukuba (JP); Takuma Minamisono, Tsukuba (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 402 days.

This patent is subject to a terminal disclaimer.

(21) Appl. No.: 12/109,959

(22) Filed: Apr. 25, 2008

(65) Prior Publication Data

US 2008/0275244 A1 Nov. 6, 2008

Related U.S. Application Data

(60) Provisional application No. 60/914,572, filed on Apr. 27, 2007.

(30) Foreign Application Priority Data

Apr. 27, 2007 (JP) ................................. 2007-118411

(51) Int. Cl.
*C07D 413/14* (2006.01)
(52) U.S. Cl. ...................................................... 546/256
(58) Field of Classification Search .................. 546/256
See application file for complete search history.

(56) References Cited

U.S. PATENT DOCUMENTS

| | | | |
|---|---|---|---|
| 4,576,956 A | 3/1986 | Makisumi et al. |
| 4,720,493 A | 1/1988 | Kawakita et al. |
| 4,785,010 A | 11/1988 | Zoller et al. |
| 5,034,393 A | 7/1991 | Hackler et al. |
| 5,070,082 A | 12/1991 | Murdock et al. |
| 5,208,247 A | 5/1993 | Trova et al. |
| 5,296,484 A | 3/1994 | Coghlan et al. |
| 5,328,921 A | 7/1994 | Trova et al. |
| 5,350,749 A | 9/1994 | Hackler et al. |
| 5,371,086 A | 12/1994 | Takemoto et al. |
| 5,691,136 A | 11/1997 | Lupski et al. |
| 5,691,336 A | 11/1997 | Dorn et al. |
| 5,710,171 A | 1/1998 | Dinsmore et al. |
| 5,747,518 A | 5/1998 | Yoshikawa et al. |
| 5,852,042 A | 12/1998 | Jakobi et al. |
| 5,945,431 A | 8/1999 | Jin et al. |
| 6,022,884 A | 2/2000 | Mantlo et al. |
| 6,080,767 A | 6/2000 | Klein et al. |
| 6,174,905 B1 | 1/2001 | Suzuki et al. |
| 6,235,728 B1 | 5/2001 | Golik et al. |
| 6,255,318 B1 | 7/2001 | Bedard et al. |
| 6,313,127 B1 | 11/2001 | Waterson et al. |
| 6,319,944 B1 | 11/2001 | Claiborne et al. |
| 6,340,690 B1 | 1/2002 | Bachand et al. |
| 6,380,218 B1 | 4/2002 | Marfat et al. |
| 6,407,116 B1 | 6/2002 | Kajino et al. |
| 6,414,013 B1 | 7/2002 | Fancelli et al. |
| 6,596,718 B1 | 7/2003 | Flohr et al. |
| 6,630,495 B1 | 10/2003 | Cooke et al. |
| 7,179,804 B2 | 2/2007 | Amegazdie et al. |
| 7,179,822 B2 | 2/2007 | Bunker et al. |
| 7,687,525 B2 | 3/2010 | Suzuki et al. |
| 7,691,882 B2 * | 4/2010 | Tanaka et al. .................. 514/333 |
| 7,754,726 B2 | 7/2010 | Lang et al. |
| 2002/0011495 A1 | 1/2002 | Clemmons |
| 2003/0045554 A1 | 3/2003 | Sankaranarayanan |
| 2003/0114491 A1 | 6/2003 | Kim et al. |
| 2003/0191158 A1 | 10/2003 | Magee |
| 2004/0038239 A1 | 2/2004 | Tsukahara et al. |
| 2004/0044040 A1 | 3/2004 | Neubert et al. |
| 2004/0152730 A1 | 8/2004 | Farina et al. |
| 2004/0198773 A1 | 10/2004 | Hart et al. |
| 2005/0119229 A1 | 6/2005 | Ammermann et al. |
| 2006/0264419 A1 | 11/2006 | Schiemann et al. |
| 2006/0270637 A1 | 11/2006 | Gravestock et al. |
| 2007/0060619 A1 | 3/2007 | Burns et al. |
| 2007/0105904 A1 | 5/2007 | Tanaka et al. |
| 2007/0105943 A1 | 5/2007 | Nakamoto et al. |
| 2007/0167493 A1 | 7/2007 | Sankaranarayanan |
| 2008/0090846 A1 | 4/2008 | Bridger et al. |

FOREIGN PATENT DOCUMENTS

| | | |
|---|---|---|
| DE | 19727117 A1 | 1/1999 |
| EP | 0124154 A2 | 7/1984 |
| EP | 0124067 A1 | 11/1984 |
| EP | 0274867 A2 | 7/1988 |
| EP | 0 326 328 A2 | 8/1989 |
| EP | 0414386 A1 | 2/1991 |
| EP | 0533130 A1 | 3/1993 |
| EP | 0976744 A1 | 2/2000 |
| EP | 1 216 980 A1 | 6/2002 |
| EP | 1217000 A1 | 6/2002 |
| EP | 1229034 A1 | 8/2002 |

(Continued)

OTHER PUBLICATIONS

European Search Report issued Jul. 29, 2010, in corresponding European Patent Application No. 05768893.9.
AKos Screening Library, Feb. 7, 2006. CAS Registry No. 434304-24-2.
Aurora Screening Library, Jan. 1, 2007, CAS Registry No. (RN): 431922-54-2.
Interchim Intermediate, Jul. 9, 2007, CAS Registry No. (RN): 438574-99-3.
Ambinter Stock Screening, Jan. 1, 2007. CAS Registry No. (RN): 764713-41-9.
Ikizler, et al, "Antimicrobial activities of some 4H-1,2,4- triazoles" Indian Journal of Pharmaceutical Sciences, 1999, vol. 61, No. 5, p. 271-274.

(Continued)

*Primary Examiner* — Patricia Morris
(74) *Attorney, Agent, or Firm* — Birch, Stewart, Kolasch & Birch, LLP

(57) ABSTRACT

There is provided a heterocycle-substituted pyridine derivative's salt or a crystal thereof. The present invention provides an acid addition salt of 3-(3-(4-(pyridin-2-yloxymethyl)-benzyl)-isoxazol-5-yl)-pyridin-2-yl amine or a crystal thereof as well as process for producing the same.

1 Claim, 6 Drawing Sheets

FOREIGN PATENT DOCUMENTS

| | | |
|---|---|---|
| EP | 1275301 A1 | 1/2003 |
| EP | 1275653 A1 | 1/2003 |
| EP | 1 369 420 A1 | 12/2003 |
| EP | 1 669 348 A1 | 6/2006 |
| EP | 1 782 811 A1 | 5/2007 |
| EP | 1 944 303 A1 | 7/2008 |
| GB | 919073 | 2/1963 |
| JP | 54-2325 A | 1/1979 |
| JP | 59-073575 | 4/1984 |
| JP | 5973575 A | 4/1984 |
| JP | 59-206353 A | 11/1984 |
| JP | 61-148178 A | 7/1986 |
| JP | 64-3162 A | 1/1989 |
| JP | 1-246264 A | 10/1989 |
| JP | 3-66689 A | 3/1991 |
| JP | 3-161470 A | 7/1991 |
| JP | 5-213877 A | 8/1993 |
| JP | 5-294935 A | 11/1993 |
| JP | 7-25853 A | 1/1995 |
| JP | 8-12579 A | 1/1996 |
| JP | 8-175993 A | 7/1996 |
| JP | 9-507245 A | 7/1997 |
| JP | 10-505600 A | 6/1998 |
| JP | 11-152275 A | 6/1999 |
| JP | 2000-504336 A | 4/2000 |
| JP | 2000-187243 | 6/2000 |
| JP | 2001-515464 A | 9/2001 |
| JP | 2001-522834 A | 11/2001 |
| JP | 2001-525365 A | 12/2001 |
| JP | 2001-527083 A | 12/2001 |
| JP | 2002-275159 | 9/2002 |
| JP | 2002-284766 A | 10/2002 |
| JP | 2002-537396 A | 11/2002 |
| JP | 2002-544162 A | 12/2002 |
| JP | 2003-506466 A | 2/2003 |
| JP | 2004-529154 | 9/2004 |
| JP | 2005-033079 | 2/2005 |
| JP | 2005-526751 A | 9/2005 |
| JP | 2006-519247 A | 8/2006 |
| WO | WO-86/03203 A1 | 6/1986 |
| WO | WO-93/12084 | 6/1993 |
| WO | WO 95/09159 A1 | 4/1995 |
| WO | WO 95/18795 A1 | 7/1995 |
| WO | WO-96/09294 A1 | 3/1996 |
| WO | WO-97/27852 | 8/1997 |
| WO | WO-97/28128 A1 | 8/1997 |
| WO | WO-98/25883 | 6/1998 |
| WO | WO-98/50029 | 11/1998 |
| WO | WO-99/24404 A1 | 5/1999 |
| WO | WO-99/48492 | 9/1999 |
| WO | WO-99/50247 | 10/1999 |
| WO | WO-00/07991 | 2/2000 |
| WO | WO-00/51998 | 9/2000 |
| WO | WO-00/62778 | 10/2000 |
| WO | WO-00/73283 | 12/2000 |
| WO | WO-01/11966 A1 | 2/2001 |
| WO | WO-01/21584 | 3/2001 |
| WO | WO-01/25181 | 4/2001 |
| WO | WO 01/26652 A1 | 4/2001 |
| WO | WO-01/27096 | 4/2001 |
| WO | WO-01/51456 | 7/2001 |
| WO | WO-01/53274 | 7/2001 |
| WO | WO-01/74779 | 10/2001 |
| WO | WO-02/00651 | 1/2002 |
| WO | WO-02/04626 A1 | 1/2002 |
| WO | WO-02/06275 | 1/2002 |
| WO | WO-02/22583 | 3/2002 |
| WO | WO-02/22583 A2 | 3/2002 |
| WO | WO-02/060875 | 8/2002 |
| WO | WO-02/060896 | 8/2002 |
| WO | WO-02/060898 | 8/2002 |
| WO | WO-02/083645 A1 | 10/2002 |
| WO | WO-02/085897 A1 | 10/2002 |
| WO | WO 03/006628 A2 | 1/2003 |
| WO | WO-03/027095 | 4/2003 |
| WO | WO-03/031435 A1 | 4/2003 |
| WO | WO 03/037860 A2 | 5/2003 |
| WO | WO-03/045385 A1 | 6/2003 |
| WO | WO 03/045920 A1 | 6/2003 |
| WO | WO-03/059903 | 7/2003 |
| WO | WO-03/068232 A1 | 8/2003 |
| WO | WO-03/068235 A1 | 8/2003 |
| WO | WO 03/068747 A1 | 8/2003 |
| WO | WO-03091226 A1 | 11/2003 |
| WO | WO-03091227 A1 | 11/2003 |
| WO | WO-2004/000813 | 12/2003 |
| WO | WO-2004/014366 A1 | 2/2004 |
| WO | WO-2004/014370 | 2/2004 |
| WO | WO-2004/029027 | 4/2004 |
| WO | WO-2004/033432 | 4/2004 |
| WO | WO-2004/048567 | 6/2004 |
| WO | WO-2004/052280 | 6/2004 |
| WO | WO-2004/089931 A1 | 10/2004 |
| WO | WO-2005/033079 | 4/2005 |
| WO | WO-2005/033079 A1 | 4/2005 |
| WO | WO-2006/016548 | 2/2006 |
| WO | WO-2006/106711 | 10/2006 |
| WO | WO-2007/052615 | 5/2007 |
| WO | WO 2007/056215 A2 | 5/2007 |
| WO | WO 2009/081970 A1 | 7/2009 |
| WO | WO-2009/084621 A1 | 7/2009 |

OTHER PUBLICATIONS

Satyanarayana, et al., "Studies on the synthesis and biological activity of 3- arylaminomethyl-5-(3-pyridyl)-1, 3, 4-oxadiazole-2-thione derivatives" Bolletino Chimico Farmaceutico, 2001, vol. 140, No. 4, p. 228-232.
Gardner et al., Nature, vol. 419, pp. 498-511, (2002).
Naik et al., J. of Biological Chemistry, vol. 278, No. 3, pp. 2036-2042, (2003).
Shinkai et al., J. Med. Chem., vol. 31, pp. 2092-2097, (1988).
Ohshima et al., J. Med. Chem., vol. 35, pp. 3402-3413, (1992).
Okawa et al., Synthesis, No. 10., pp. 1467-1475 (1998).
European Search Report issued Jul. 19, 2010, in corresponding European Patent Application No. 06730370.1.
Pernak, J. et al., "Synthesis and antimicrobial activities of new pyridinium and benzimidazolium chlorides," Eur. J. Med. Chem., vol. 36 (2001) pp. 313-320.
Pregnolato, M. et al., "3H-[1,2]Dithiolo[3, 4-b]pyridine-3-thione and its derivatives Synthesis and antimicrobial activity," IL Farmaco, vol. 55, (2000) pp. 669-679.
Connors et al., "Prodrugs in medicine," Overview Biologicals & Immunologicals, Exp. Opin. Ther. Patents, vol. 5, No. 9, 1995, pp. 873-885.
Supplementary European Search Report dated Feb. 6, 2009 for corresponding European Application No. 04788159.4.
International Search Report dated May 20, 2008 for corresponding International Application No. PCT/JP2008/057851.
Chang, K. Y. et al., "Synthesis and Structure-Activity Relationships of Quaternary Ammonium Cephalosporins with 3-Pyrazolylpyridinium Derivatives," Bioorganic & Medicinal Chemistry Letters (2000) vol. 10, No. 11, pp. 1211-1214.
Plate, R. et al., "Synthesis and Muscarinic Activities of 3-(Pyrazolyl)-1,2,5,6-tetrahydropyridine Derivatives," Bioorganic & Medicinal Chemistry Letters (1996) vol. 10, No. 2, pp. 227-237.
Vrzheschch, P. V. et al., "Supercooperativity in platelet aggregation: Substituted pyridyl isoxazoles, a new class of supercooperative platelet aggregation inhibitors," FEBS Letters (1994) vol. 351, No. 2, pp. 168-180.
Lukevics, E. et al., "Synthesis and cytotoxicity of silyl- and carbonyl-substituted isoxazoles," Chemistry of Heterocyclic Compounds (2000) vol. 36, No. 10, pp. 1226-1231.
Chemcats, Interchim Intermediates, STK030913, Pyridine, 3-[3-[(4-methoxyphenyl)methyl]-1,2,4-oxadiazol-5-yl]-, 438574-99-3, Jul. 9, 2007, 2020895193.
Chemcats, Akos Screening Library, AKL-P-1720927, Pyridine, 3-[5-[(2-methoxyphenyl)methyl]-1,2,4-oxadiazol-3-yl]-434304-24-2, Feb. 7, 2006, 2021278791.
Chan, L., et al., Database Crossfire Beilstein: Beilstein Institute Zur Foerderung Der Chemischen Wissenschaften; XP-002512523; Database accession No. 8422493 (1999).
Okawa T., et al., "Pyrido [2, 3-d] pyrimidine derivatives. Synthesis via intermolecular aza-Wittig reaction/heterocyclization and the crystal structure", Database CA [Online] Chemical Abstract Service; XP002512524; Database accession No. 677971 (1998).

Kajino M., et al., "Preparation and formulation of quinazoline derivatives as allergy inhibitors", Database CA [Online], Chemical Abstract Service; XP002512525 Database accession No. 216905 (1999).

Piechaczek J., et al., "Monoamine oxidase inhibitors. VII. Derivatives of quinolinecarboxylic acids", Database CA [Online], Chemical Abstract Service; XP002512526 Database accession No. 75701 (1966).

Modena T., et al., "Plant growth regulating activities of 2-[2-(arylamino)-2-oxoethyl] benzoic acids", Database CA [Online], Chemical Abstract Service; XP002512527 Database accession No. 597690 (1993).

Chemcats, Aurora Screening Library, , kbsa-0118093, Pyridine, 3-[5-[(4-methoxyphenyl)methyl]-1,2,4-oxadiazol-3-yl]-, 431922-54-2, Jan. 1, 2007; 2025867145.

Chemcats, Ambinter Stock Screening Collection, STK143803, Pyridine, 3-[5-[(4-methoxyphenyl)methyl]-1,2,4-thiadiazol-2-yl]-, 764713-41-9, Jun. 1, 2007, 2036647688.

An Office Action from co-pending U.S. Appl. No. 10/573,890, mailed Jul. 29, 2009.

Guillory, "Generation of Polymorphs, Hydrates, Solvates, and Amorphous Solids", *Polymorphism in Pharmaceutical Solids*, 1999, pp. 183-226, ed. Harry G. Brittain, Marcel Dekker, Inc., New York.

Ishikawa et al., "TAK-599, a Novel N-Phosphono Type Prodrug of Anti-MRSA Cephalosporin T-91825: Synthesis, Physiochemical and Pharmacological Properties", Bioorganic & Medicinal Chemistry, vol. 11, 2003, 2427-2437, Elsevier Science Ltd.

Tanaka et al., "An Effective Lewis Acid-Mediated 1,3-Dipolar Cycloaddition of Nitrile Oxide Using Acetylene: Synthesis of a (2-Aminopyridin-3-yl) isoxazole Derivative and Its Application to Novel Antifungal Agents," pp. 1-8.

Vippagunta et al., "Crystalline Solids", Advanced Drug Delivery Reviews, 2001, pp. 3-26, vol. 48.

Office Action issued May 7, 2009 in co-pending U.S. Appl. No. 11/589,128.

Chan et al., "Discovery of 1,6-Naphthylridines as a Novel Class of Potent and Selective Human Cytomegalovirus Inhibitors," Journal of Medicinal Chemistry (1999), vol. 42, No. 16, pp. 3023-3025.

Kushner et al., "Experimental Chemotherapy of Tuberculosis. II. The Synthesis of Pyrazinamides and Related Compounds," Journal of the American Chemical Society (1952), vol. 74, pp. 3617-3621.

Lucas et al., "Facile Synthesis of a Library of 9-Alkyl-8-benzyl-9H-purin-6-ylamine Derivatives," Journal of Combinatorial Chemistry (2001), vol. 3, No. 6, pp. 518-520.

Tanaka et al., "An Effective Synthesis of a (Pyridin-3-yl)isoxazole via 1,3-Dipolar Cycloaddition Using ZnCl2: Synthesis of a (2-Aminopyridin-3-yl)isoxazole Derivative and its Antifungal Activity," Chemistry Letters, vol. 39, No. 10, pp. 1033-1035, The Chemical Society of Japan, Oct. 5, 2010.

Database Chemcats [Online] Chemical Abstracts Service, Columbus, Ohio, US; XP002600785 Database accession No. 2059288788 *Order Number (ON): 6700755* & Chembridge Corporation: "ChemBridge Screening Library" Jun. 9, 2010, ChemBridge Corporation, San Diego (USA).

Database Chemcats [Online] Chemical Abstracts Service, Columbus, Ohio, US; XP002600787 Database accession No. 2084604173 *Order Number (ON): STK143803* & Vitas-M: "Vitas-M Screening Collection" Jul. 13, 2010, Vitas-M, Hodynski Blv. 15, Moskow, (RU).

Database Registry [Online] Chemical Abstracts Service, Columbus, Ohio, US; Jul. 16, 2002, XP002600783 Database accession No. 438574-99-3(RN).

Database Registry [Online] Chemical Abstracts Service, Columbus, Ohio, US; Jun. 18, 2002, XP002600784 Database accession No. 431922-54-2(RN) *abstract*.

Database Registry [Online] Chemical Abstracts Service, Columbus, Ohio, US; Oct. 18, 2004, XP002600786 Database accession No. 764713-41-9(RN) *abstract*.

Extended European Search Report dated Oct. 11, 2010, issued in corresponding European Patent Application No. 07828273.8.

Chandran et al., "Synthesis of 8-Aminoquinolines; Part II—8-Guidance Derivatives," Journal of Scientific & Industrial Research (1952), 11B, pp. 129-132.

Hata, "New Approaches to Antifungal Drugs for the Treatment of Fungal and Protozoal Infections, Ravuconazole and Beyond: New Targets and Pre-clinical Strategies," The SMI's 12th Annual Conference, Superbugs and Superdrugs, Mar. 18, 2010, Crowne Plaza London—St. James, 44 pages.

Lo et al., "Development of highly selective and sensitive probes for hydrogen peroxide," Communication. Chem Comm. The Royal Society of Chemisty, 2003, pp. 2726-2729.

U.S. Office Action dated May 14, 2010 for U.S. Appl. No. 11/887,249.

US. Office Action issued May 4, 2010 for copending Application No. 11/658,901.

English language machine generated translation for JP-7-25853-A, dated Jan. 27, 1995.

Japanese Office Action, dated Aug. 6, 2010, for Japanese Patent Application No. 2005-514417.

US Office Action, dated Oct. 13, 2010. for U.S. Appl. No. 11/558,901.

Extended European Search Report issued Apr. 18, 2011, in European Patent Application No. 08740624.5.

Response to Communication Pursuant to Rules 70(2) and 70a(s) EPC, dated May 6, 2011, issued in European Patent Application No. 08 740 624.5.

Freshney et al., Culture of Animal Cells, A Manual of Basic Technique, 1983, Wiley & Sons, Inc., New York pp. 7-9.

Office Action issued Jun. 17, 2011, in related U.S. Appl. No. 12/109,834.

Office Action issued Jun. 22, 2011, in Chinese Patent Application No. 200880007023.8, with English translation.

Office Action issued Jul. 11, 2011, in U.S. Appl. No. 12/343,889.

* cited by examiner

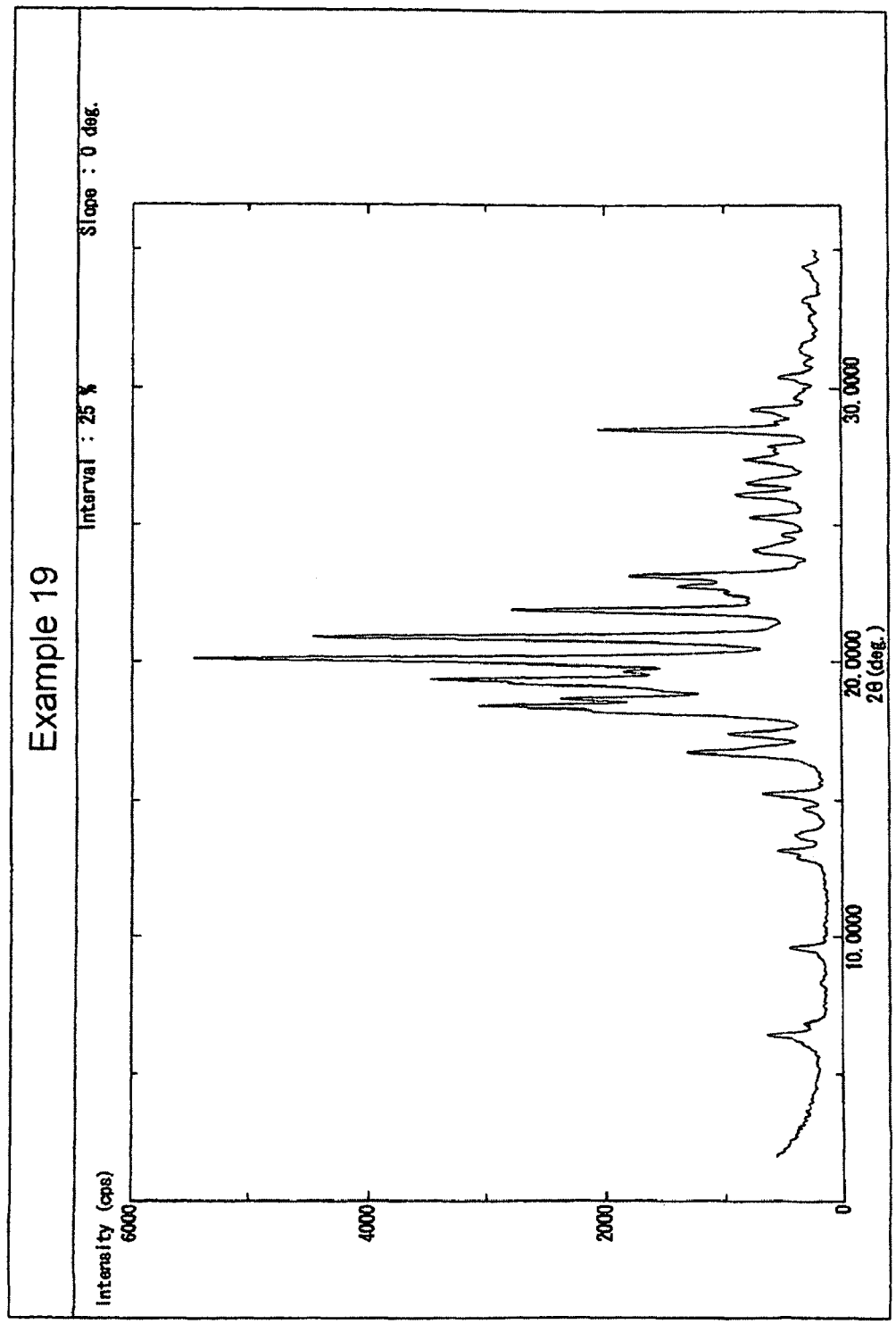

HETEROCYCLE-SUBSTITUTED PYRIDINE DERIVATIVE'S SALT OR CRYSTAL THEREOF

This Nonprovisional application claims priority under 35 U.S.C. §119(e) on U.S. Provisional Application No(s). 60/914,572 filed on Apr. 27, 2007 and under 35 U.S.C. §119(a) on Patent Application No(s). 2007-118411 filed in Japan on Apr. 27, 2007. The entire contents of all are hereby incorporated by reference.

TECHNICAL FIELD

The present invention relates to a heterocycle-substituted pyridine derivative's salt or crystal thereof, which 1) acts against the onset, development and persistence of infections by inhibiting fungal GPI (glycosylphosphatidyl-inositol) biosynthesis, thereby inhibiting expression of cell wall proteins and blocking cell wall assembly while preventing the fungus from attaching to cells so that the pathogen cannot become pathogenic, and 2) is superior in terms of physical properties, safety and metabolic stability, and is extremely useful as a preventive or therapeutic agent for fungal infections. More specifically, the present invention relates to an acid addition salt of 3-(3-(4-(pyridin-2-yloxymethyl)-benzyl)-isoxazol-5-yl)-pyridin-2-ylamine (the following formula (1); hereinafter referred to as "Compound 1") or a crystal thereof.

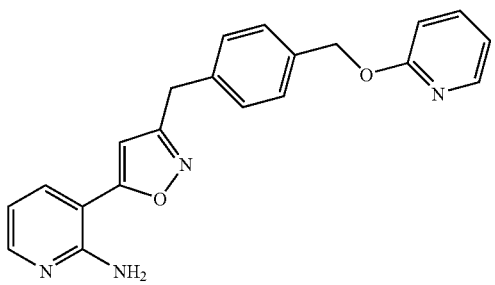

BACKGROUND ART

In recent years, managements of opportunistic infections have become more and more significant more than ever because of an increase in the number of elderly people and immunocompromised patients as a result of advanced chemotherapies or the like. As demonstrated by the fact that opportunistic infections are occurring one after another by different avirulent pathogen, it is shown that the problem of infectious disease will not ends as long as there are underlying diseases that diminish the immune functions of patients. Consequently, new strategies for infectious diseases control, including the problem of drug-resistant pathogen, will be one of the important issues in the soon-to-come aged society.

In the field of antifungal agents, heretofore, for instance, amphotericin B which is based on a polyene skeleton, fluconazole, itraconazole and voriconazole which are based on an azole skeleton, or the like, have been developed for the treatment of deep seated mycoses. Most of pre-existing drugs already available commercially have similar mechanism of action, and currently, the appearance of azole-resistant fungi or the like has been problems.

In recent years, as a 1,3-β-glucan synthetase inhibitor with a novel mechanism, naturally occurring compound-derived cyclic hexapeptides caspofungin and micafungin or the like, have been developed; however, from the fact that these agents only exist in injectable form, they are not yet sufficient practically as antifungal agents.

Since there have been the situations that the pre-existing antifungal agents are insufficient for treatment of the deep seated mycoses, there is a demand and need for development of agents which are based on a novel mechanism and are of high safety.

As the related art relevant to antifungal agents based on such a novel mechanism, Patent Documents 1 and 2 describe pyridine derivatives which demonstrates effects against the onset, progress, and persistence of infections by inhibiting the expression of cell wall proteins, inhibiting the cell wall assembly and also adhesion onto cells, and preventing pathogens from showing pathogenicity, with the process which transports GPI-anchored proteins to the cell wall being inhibited.

However, groups of the compounds disclosed in Patent Document 1 have 2-benzyl pyridine moieties as the common structure, clearly differing structurally from compounds according to the present invention. In addition, the groups of the compounds disclosed in Patent Document 1 bear the problem that, although these compounds demonstrate activities in vitro, they are easily metabolized inside the body. The group of compounds disclosed in Patent Document 2 exhibits excellent antifungal activity, but the group of representative compounds has the structure represented by the following formula:

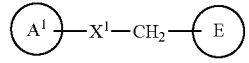

$A^1$ = optionally substituted 3-pyridyl or quinolyl, etc.
$X^1$ = —C(=O)—NH, —NH—C(=O)—, etc.
E = furyl, thienyl, pyrrolyl, phenyl, pyridyl, tetrazolyl, thiazolyl, or pyrazoly Looking only at those having pyridine ring skeletons, this group differs structurally from the compounds according to the present invention in that the common structure has a single ring bound via an amidemethylene linker at the pyridine ring 3-position.

Patent Documents 3 to 5 also provide examples of related art with structures similar to the compounds according to the present invention. Patent Documents 3 and 4 describe pyridine derivatives substituted by a pyrazole ring, which are used as glycine transporter inhibitors or 5-HT receptor ligands, while Patent Document 5 describes 5-member heterocyclic substituted pyridine derivatives which are used as an AGE disruptor and inhibitor.

However, Patent Documents 3 to 5 do not disclose the compounds according to the present invention, and the antifungal effects of the compounds disclosed in Patent Documents 3 to 5 against *Candida, Aspergillus, Cryptococcus* and the like which are common fungi in human fungal disease are not disclosed.

[Patent Document 1] International Publication WO 02/04626 pamphlet
[Patent Document 2] International Publication WO 05/033079 pamphlet
[Patent Document 3] International Publication WO 03/031435 pamphlet
[Patent Document 4] International Publication WO 04/089931 pamphlet
[Patent Document 5] International Publication WO 02/085897 pamphlet

DISCLOSURE OF INVENTION

Problems to be Solved by the Invention

An object of the present invention is to provide a heterocycle-substituted pyridine derivative salt or crystal thereof having excellent antimycotic action not found in conventional antifungal agents, useful as an antifungal agent that is excellent in the aspects of physical properties, safety and metabolic stability, excellent in the aspect of physical properties, and highly useful as medicinal drug product, and preparation method thereof.

Means for Solving the Problems

In order to achieve the above object, the present invention provides:
<1> an acid addition salt of 3-(3-(4-(pyridin-2-yloxymethyl)-benzyl)-isoxazol-5-yl)-pyridin-2-yl amine, wherein said acid is selected from the group consisting of hydrochloric acid, hydrobromic acid, phosphoric acid, sulfuric acid, methanesulfonic acid, ethanesulfonic acid, benzenesulfonic acid, p-toluenesulfonic acid, fumaric acid, maleic acid, succinic acid and citric acid.

Advantageous Effect of the Invention

The heterocycle-substituted pyridine derivative's salt or crystal thereof according to the present invention 1) acts against the onset, development and persistence of infections by inhibiting fungal GPI biosynthesis, thereby inhibiting expression of cell wall proteins and blocking cell wall assembly while preventing the fungus from attaching to cells so that the pathogen cannot become pathogenic, and 2) is superior in terms of physical properties, safety and metabolic stability, and is extremely useful as a preventive or therapeutic agent for fungal infections.

BRIEF DESCRIPTION OF THE DRAWINGS

FIG. 6 shows the X-ray diffraction pattern of the free-form anhydride (TYPE I) of 3-(3-(4-(pyridin-2-yloxymethyl)-benzyl)-isoxazol-5-yl)-pyridin-2-ylamine obtained in Example 19 of the present invention.

BEST MODE FOR CARRYING OUT THE INVENTION

Figure 1:
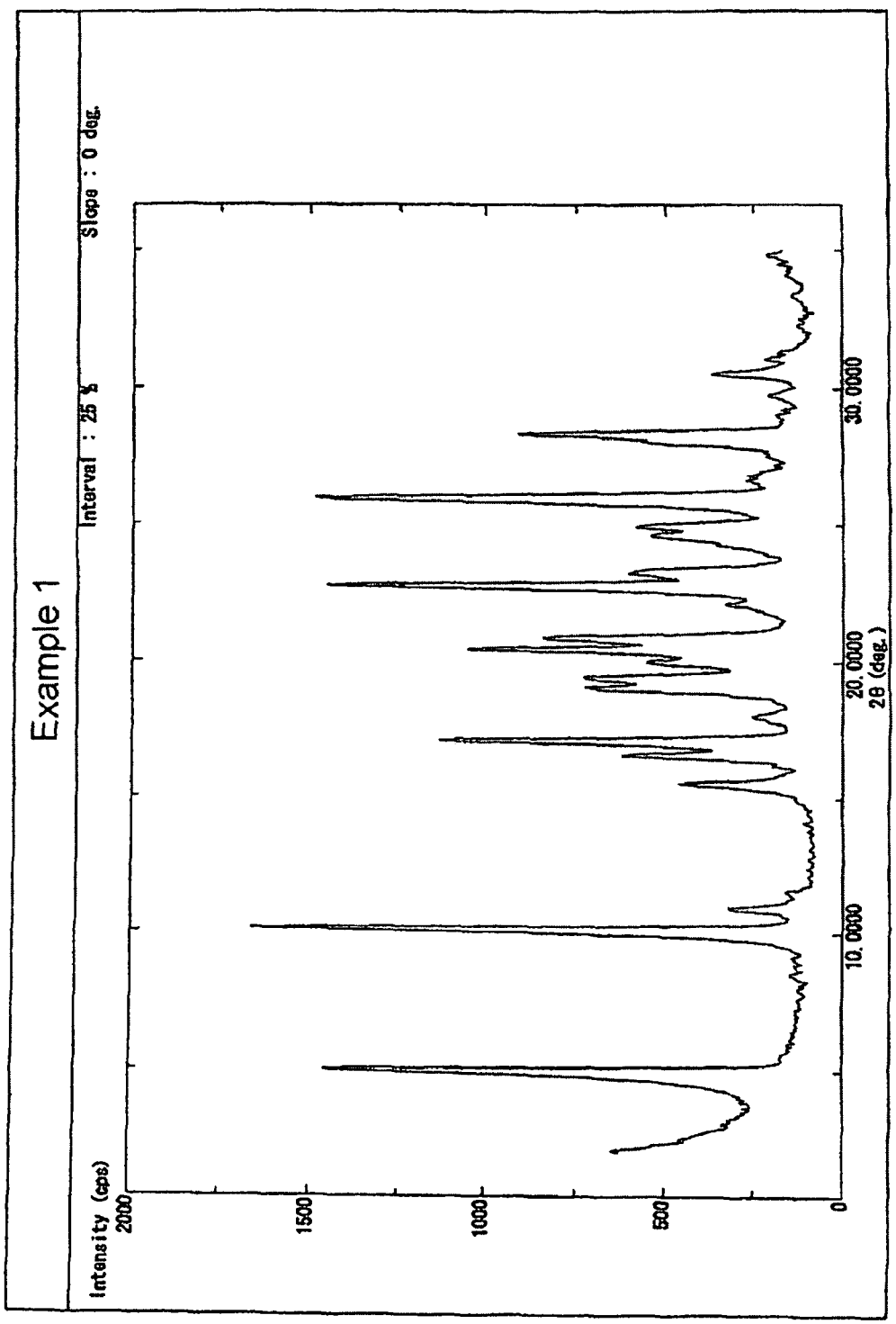
FIG. 1 shows the X-ray diffraction pattern of 3-(3-(4-(pyridin-2-yloxymethyl)-benzyl)-isoxazol-5-yl)-pyridin-2-ylamine hydrochloride anhydride obtained in Example 1 of the present invention.

Hereinafter, the content of the present invention will be described in detail. The acid addition salt according to the present invention is an acid addition salt of 3-(3-(4-(pyridin-2-yloxymethyl)-benzyl)-isoxazol-5-yl)-pyridin-2-ylamine (Compound 1), in which the acid is hydrochloric acid, hydrobromic acid, phosphoric acid, sulfuric acid, nitric acid, methanesulfonic acid, ethanesulfonic acid, benzenesulfonic acid, p-toluenesulfonic acid, fumaric acid, maleic acid, succinic acid, citric acid, malic acid or trifluoroacetic acid. Note that the acid addition salt according to the present invention may be a non-solvate or a solvate such as a hydrate, and the number of molecules added is also not limited, and for instance, 0.5 molecules, 1 molecule, or 2 molecules may be added. In addition, the acid addition salt according to the present invention not only includes crystals, but also amorphous of acid addition salt of Compound 1.

More specifically, the crystal of the present invention include 1) a crystal of hydrochloride of 3-(3-(4-(pyridin-2-yloxymethyl)-benzyl)-isoxazol-5-yl)-pyridin-2-ylamine (Compound 1; idem hereinafter), 2) a crystal of dihydrochloride of Compound 1, 3) a crystal of hydrobromide of Compound 1, 4) a crystal of dihydrobromide of Compound 1, 5) a crystal of phosphate of Compound 1, 6) a crystal of hemisulfate of Compound 1, 7) a crystal of disulfate of Compound 1, 8) a crystal of methanesulfonate salt of Compound 1, 9) a crystal of dimethanesulfonate salt of Compound 1, 10) a crystal of ethanesulfonate of Compound 1, 11) a crystal of benzenesulfonate of Compound 1, 12) a crystal of p-toluenesulfonate of Compound 1, 13) a crystal of hemifumarate of Compound 1, 14) a crystal of maleate of Compound 1, 15) a crystal of hemisuccinate of Compound 1 or 16) a crystal of citrate of Compound 1.

The crystal of hydrochloride anhydride of Compound 1 according to the present invention has diffraction peaks at diffraction angles (2θ±0.2°) of 5.04, 10.16, 16.56, 17.10, 20.42, 20.82, 22.76, 25.96 and 28.30 in a powder X-ray diffraction, and preferably, has diffraction peaks at 5.04, 10.16 and 17.10.

The crystal of hemisulfate anhydride of Compound 1 according to the present invention has diffraction peaks at diffraction angles (2θ±0.2°) of 7.28, 9.44, 15.98, 16.64, 20.00, 20.32, 21.00, 21.46, 21.78 and 22.46 in a powder X-ray diffraction, and preferably, has diffraction peaks at 16.64, 20.00 and 20.32.

The crystal of methane sulfonate anhydride of the Compound 1 according to the present invention has diffraction peaks at diffraction angles (2θ±0.2°) of 15.06, 15.96, 16.46, 17.06, 19.52, 19.96, 21.92, 23.86, 26.84 and 27.12 in a powder X-ray diffraction, and preferably, has diffraction peaks at 16.46, 21.92, 26.84 and 27.12.

The crystal of citrate anhydride of Compound 1 according to the present invention has diffraction peaks at diffraction angles (2θ±0.2°) of 4.26, 8.30, 8.58, 10.40, 17.22, 18.40, 20.20, 23.42, 23.92 and 24.12 in a powder X-ray diffraction, and preferably, has diffraction peaks at 4.26, 17.22 and 18.40.

The crystal of a free-form anhydride Compound 1 according to the present invention (TYPE I) has diffraction peaks at diffraction angles (2θ±0.2°) of 6.36, 9.60, 16.76, 18.44, 18.70, 19.06, 19.38, 20.10, 20.90 and 21.94 in a powder X-ray diffraction, and preferably, has diffraction peaks at 9.60, 20.10 and 20.90.

The crystal of a free-form anhydride Compound 1 according to the present invention (TYPE II) has diffraction peaks at diffraction angles (2θ±0.2°) of 11.26, 15.28, 15.90, 16.12, 16.94, 17.36, 19.58, 19.80, 20.82 and 22.94 in a powder X-ray diffraction, and preferably, has diffraction peaks at 11.26, 17.36 and 20.82.

Since, in general, errors in the diffraction angle (2θ) may occur within a range of ±0.2° in a powder X-ray diffraction, it must be understood that the above values of diffraction angles include those numbers within a range of on the order of ±0.2°. Therefore, the present invention includes not only those crystals with totally matching diffraction angles in a powder X-ray diffraction, but also those crystals with matching diffraction angles within an error margin of ±0.2°.

When using the crystals according to the present invention as a drug, in general, the crystal according to the present invention and suitable additives are blended into the formulation for use. With the proviso that the above does not deny the use of the crystal according to the present invention in the original form directly as a drug.

Examples of additives include, diluents, binders, lubricants, disintegrating agents, colorants, flavoring agents, emulsifiers, surfactants, solubilizing agents, suspending agents, isotonizing agents, buffering agents, antiseptic agents, antioxidants, stabilizers, absorption promoters, and the like, which are used generally for the drug. According to need, these can also be suitably combined for use.

Examples of the above-mentioned diluents include lactose, sucrose, fructose, corn starch, mannitol, sorbitol, starch, gelatinized starch, dextrin, crystalline cellulose, light anhydrous silicic acid, aluminum silicate, calcium silicate, magnesium aluminometasilicate, calcium hydrogen phosphate, and the like.

Examples of the above-mentioned binders include polyvinyl alcohol, methylcellulose, ethylcellulose, gum arabic, tragacanth, gelatin, shellac, hydroxypropyl methylcellulose, hydroxypropyl cellulose, sodium carboxymethyl cellulose, polyvinylpyrrolidone, macrogol, and the like.

Examples of the above-mentioned lubricant include magnesium stearate, calcium stearate, sodium stearyl fumarate, talc, polyethyleneglycol, colloidal silica, and the like.

Examples of the above-mentioned disintegrating agents include crystalline cellulose, agar, gelatin, calcium carbonate, sodium bicarbonate, calcium citrate, dextrin, pectin, low-substituted hydroxypropyl cellulose, carboxymethyl cellulose, calcium carboxymethyl cellulose, crosscarmellose sodium, carboxymethyl starch, sodium carboxymethyl starch, and the like.

Examples of the above-mentioned colorant include iron sesquioxide, yellow ferric oxide, carmine, caramel, β-carotene, titanium oxide, talc, riboflavin phosphate sodium and yellow aluminum lake, for which the addition is pharmaceutically allowed.

Examples of the above-mentioned flavoring agents include cocoa powder, menthol, aromatic powder, peppermint oil, borneol, cinnamon powder, and the like.

Examples of the above-mentioned emulsifiers or surfactants include stearyl triethanolamine, sodium lauryl sulfate, lauryl aminopropionic acid, lecithin, glyceryl monostearate, sucrose fatty acid ester, glycerin fatty acid ester, and the like.

Examples of the above-mentioned solubilizing agents include polyethyleneglycol, propylene glycol, benzyl benzoate, ethanol, cholesterol, triethanolamine, sodium carbonate, sodium citrate, Polysorbate 80, nicotinic acid amide, and the like.

Examples of the above-mentioned suspending agents include hydrophilic macromolecules, such as polyvinyl alcohol, polyvinyl pyrrolidone, methyl cellulose, hydroxymethyl cellulose, hydroxyethyl cellulose and hydroxypropyl cellulose, in addition to the above surfactants described above.

Examples of the above-mentioned isotonizing agents include fructose, sodium chloride, mannitol, sorbitol, and the like.

Examples of the above-mentioned buffering agents include buffering solution of phosphate, acetate, carbonate, citrate, and the like.

Examples of the above-mentioned antiseptic agents include methyl paraben, propyl paraben, chlorobutanol, benzyl alcohol, phenetyl alcohol, dehydro acetic acid, sorbic acid, and the like.

Examples of the above-mentioned antioxidants include sulfite, ascorbic acid, α-tocopherol, and the like.

In addition, examples of the above-mentioned formulation include peroral formulations, such as, tablet, powder, granule, capsule, syrup, troche and inhalant; formulations for external use, such as, suppository, ointment, eye ointment, tape, eye drop, nose drop, ear drop, cataplasm and lotion, or injectables.

The above-mentioned peroral formulations are formulated by combining suitably the above additives. Note that the surface thereof may be coated as necessary.

The above-mentioned formulations for external use are formulated by suitably combining among the above additives, in particular, the diluents, the binders, the flavoring agents, the emulsifiers, the surfactants, the solubilizing agents, the suspending agents, the isotonizing agents, the antiseptic agents, the antioxidants, the stabilizers and the absorption promoters.

The above-mentioned injectables are formulated by suitably combining among the above additives, in particular, the emulsifiers, the surfactants, the solubilizing agents, the suspending agents, the isotonizing agents, the buffering agents, the antiseptic agents, the antioxidants, the stabilizers and the absorption promoters.

When the salt or crystal according to the present invention is used as a drug, although the amount thereof used differs depending on symptoms and age, in general, from 0.1 mg to 10 g (preferably from 1 mg to 2 g) for the peroral formulation, from 0.01 mg to 10 g (preferably from 0.1 mg to 2 g) for the formulation for external use and from 0.01 mg to 10 g (preferably from 0.1 mg to 2 g) for the injectable, is administered once, or is used divided into 2 to 4 times, daily.

EXAMPLES

The salt of the compound according to the present invention or the crystal thereof can be prepared by the methods described in, for instance, the following Reference Examples, Manufacturing Examples, and Examples. However, these are illustrative, and the compound according to the present invention is not limited to the following specific examples in any circumstances.

Reference Example 1

3-(3-(4-(Pyridin-2-yloxymethyl)-benzyl)-isoxazol-5-yl)-pyridin-2-yl amine

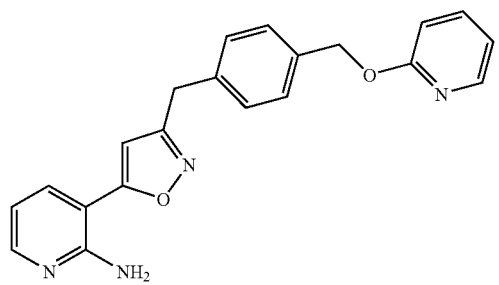

To a solution of (4-(pyridin-2-yloxymethyl)-phenyl)-acetohydroxymoyl chloride described in Preparation Example 1-3-5 (510 mg, 1.84 mmol) and 3-ethinyl-pyridin-2-ylamine described in Preparation Example 1-1-3 (150 mg, 1.27 mmol) in tetrahydrofuran (5 mL) was added triethylamine (708 μL, 5.08 mmol) at room temperature, which was stirred at room temperature for 95 minutes. To the reaction solution was added water at room temperature and extracted with ethyl acetate. The organic layer was washed with saturated sodium chloride water, this was dried over anhydrous magnesium sulfate, and the solvent thereof was evaporated under a reduced pressure. The residue was purified by NH silica gel column chromatography (heptane:ethyl acetate=2:1) to obtain the title compound (120 mg).

$^1$H-NMR Spectrum (CDCl$_3$) δ (ppm): 4.08 (2H,s), 5.37 (2H,s), 6.33 (1H,s), 6.45 (2H,brs), 6.79-6.82 (2H,m), 6.88-6.91 (1H,m), 7.30 (2H,d,J=8.1 Hz), 7.45 (2H,d,J=8.1 Hz), 7.57-7.61 (1H,m), 7.85 (1H,d, J=7.3 Hz), 8.03 (1H,d,J=5.5 Hz), 8.17 (1H,m).

The starting material, 3-ethinyl-pyridin-2-ylamine, was synthesized according to the following methods.

Preparation Example 1-1-1

2,2-Dimethyl-N-pyridin-2-yl-propionamide

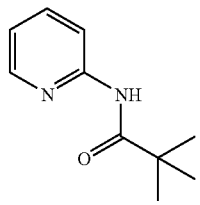

To a solution of 2-aminopyridine (50.0 g, 531 mmol) in methylene chloride (500 mL) were added triethylamine (81.4 mL, 584 mmol) and pivaloyl chloride (71.9 mL, 584 mmol) at 0° C, which was stirred at room temperature for 4 hours 30 minutes. The reaction solution was partitioned in water and methylene chloride. The organic layer was washed with water and saturated sodium chloride water, dried over anhydrous magnesium sulfate, and the solvent thereof was evaporated under a reduced pressure. To a solution of the resulting residue in methanol (300 mL) was added potassium carbonate (73.4 g, 531 mmol) at 0° C, which was stirred at room temperature for 90 minutes. The reaction solution was partitioned into water and ethyl acetate at room temperature. The organic layer was washed with saturated sodium chloride water, dried over anhydrous magnesium sulfate, and the solvent thereof was evaporated under a reduced pressure. To the residue was added heptane (300 mL), and the deposited solid was recovered by filtration to obtain title compound (80.2 g). Furthermore, the filtrate was concentrated under a reduced pressure, the residue was purified by silica gel column chromatography (heptane:ethyl acetate=2:1) to obtain the title compound (12.2 g).

$^1$H-NMR Spectrum (DMSO-d$_6$) δ (ppm): 1.22 (9H,s), 7.06-7.09 (1H,m), 7.72-7.77 (1H,m), 8.01-8.03 (1H,m), 8.29-8.31 (1H,m), 9.71 (1H,s).

Preparation Example 1-1-2

N-(3-iodo-pyridin-2-yl)-2,2-dimethyl-propionamide

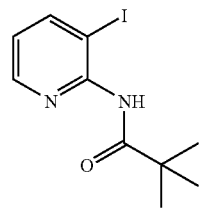

To a mixture of 2,2-dimethyl-N-pyridin-2-yl-propionamide described in Preparation Example 1-1-1 (3.0 g, 17 mmol), N,N,N',N'-tetramethyl ethylenediamine (6.3 mL, 42 mmol) and tetrahydrofuran (60 mL) was added n-butyl lithium (1.6M n-hexane solution, 30 mL, 47 mmol) dropwise at −78° C, which was stirred overnight at 0° C. To the reaction mixture was added iodine (6.8 g, 27 mmol) at −78° C, which was stirred at 0° C for 1.5 hours. To the reaction mixture were added water and a saturated aqueous solution of sodium thiosulfate, and extracted with ethyl acetate. The organic layer was washed with saturated sodium chloride water, and the solvent thereof was evaporated under a reduced pressure. The residue was purified by silica gel column chromatography (ethyl acetate:heptane=2:1) to obtain the title compound (2.9 g).

$^1$H-NMR Spectrum (CDCl$_3$) δ (ppm): 1.38 (9H,s), 6.85 (1H,dd,J=4.8,7.9 Hz), 7.94 (1H,brs), 8.11 (1H,dd,J=1.7,7.9 Hz), 8.46 (1H,dd,J=1.7,4.6 Hz).

Preparation Example 1-1-3

3-Iodo-pyridin-2-ylamine

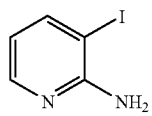

Under refluxing, a mixture of N-(3-iodo-pyridin-2-yl)-2,2-dimethyl-propionamide described in Preparation Example 1-1-2 (66.2 g, 218 mmol), an aqueous solution of 5N sodium hydroxide (200 mL) and methanol (200 mL), was stirred for one hour and 20 minutes. The reaction solution was allowed to room temperature and partitioned into water and ethyl acetate. The aqueous layer was extracted three times with ethyl acetate. The organic layers were combined, washed with saturated sodium chloride water, and this was dried over anhydrous sodium sulfate. Sodium sulfate was removed by filtration, and the solvent thereof was concentrated under a reduced pressure to obtain the title compound (41.2 g).

$^1$H-NMR Spectrum (DMSO-d$_6$) δ (ppm): 6.00 (2H,brs), 6.32 (1H,dd, J=4.8,7.2 Hz), 7.87 (1H,d,J=7.2 Hz), 7.92 (1H, d,J=4.8 Hz).

Preparation Example 1-1-4

3-Trimethylsilanyl ethinyl-pyridin-2-ylamine

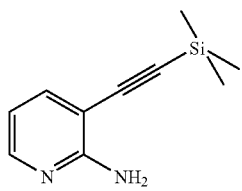

To a mixture of 3-iodo-pyridin-2-ylamine described in Preparation Example 1-1-3 (40.2 g, 183 mmol), trimethylsilyl acetylene (51.7 mL, 366 mmol), copper(I) iodide (3.49 g, 18.3 mmoL), N,N-diisopropyl ethyl amine (63.7 mL, 366 mmol), N-methylpyrrolidinone (200 mL) was added tetrakis (triphenyl phosphine) palladium (0) (10.6 g, 9.15 mmol), which was stirred at room temperature for 3 hours 10 minutes under a nitrogen stream. To the reaction solution was added water and extracted four times with ethyl acetate. The solvent thereof was concentrated under a reduced pressure. The residue was purified by NH silica gel chromatography (heptane:ethyl acetate=4:1). The resulting solution was concentrated under a reduced pressure and the residue was purified by silica gel chromatography (heptane:ethyl acetate=2:1 then 1:1) to obtain the title compound (28.1 g).

$^1$H-NMR Spectrum (DMSO-$d_6$) δ (ppm) 0.25 (9H,s), 6.09 (2H,brs), 6.51-6.57 (1H,m), 7.50-7.55 (1H,m), 7.95-7.99 (1H,m).

Preparation Example 1-1-5

3-Ethinyl-pyridin-2-ylamine

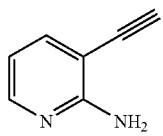

To a solution of 3-trimethylsilanyl ethinyl-pyridin-2-ylamine described in Preparation Example 1-1-4 (28.1 g, 148 mmoL) in tetrahydrofuran (300 mL) was added tetrabutyl ammonium fluoride (1M tetrahydrofuran solution, 20 mL, 20 mmol), which was stirred at room temperature for 15 minutes. To the reaction solution was added water and extracted four times with ethyl acetate. The organic layer was dried over anhydrous sodium sulfate, and the solvent thereof was evaporated under a reduced pressure. The residue was purified by silica gel chromatography (heptane:ethyl acetate=1:1 then 1:2) to obtain the title compound (16.4 g).

$^1$H-NMR Spectrum (DMSO-$d_6$) δ (ppm): 4.43 (1H,s), 6.14 (2H,brs), 6.53 (1H,dd, J=4.8,7.2 Hz), 7.53 (1H,d,J=7.2 Hz), 7.96 (1H,d,J=4.8 Hz).

Preparation Example 1-2-1

3-Trimethylsilanyl ethinyl-pyridin-2-yl amine (Alternative Method)

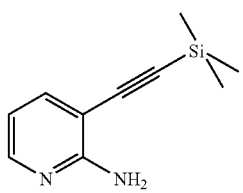

To a solution of 2-amino-3-bromopyridine (5.72 g, 33.1 mmol) in N-methylpyrrolidinone (120 mL) were added trimethylsilyl acetylene (9.36 mL, 66.2 mmol), tetrakis(triphenyl phosphine) palladium (0) (1.91 g, 1.66 mmol), copper (I) iodide (630 mg, 3.31 mmol) and N,N-diisopropyl ethyl amine (11.5 mL, 66.2 mmol) at room temperature, which was stirred at 70° C for 6 hours under a nitrogen atmosphere. To the reaction solution was added water, and extracted with ethyl acetate. The organic layer was washed with water and saturated sodium chloride water, dried over anhydrous magnesium sulfate, and the solvent thereof was evaporated under a reduced pressure. The residue was purified by silica gel column chromatography (heptane:ethyl acetate=2:1) to obtain the title compound (5.94 g).

The starting material, (4-(pyridin-2-yloxymethyl)-phenyl)-acetohydroxymoyl chloride, was synthesized according to the following methods.

Preparation Example 1-3-1

(4-(Pyridin-2-yloxymethyl)-phenyl)methanol

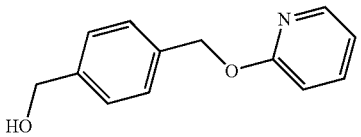

To a mixture of 1,4-benzenedimethanol (5.5 g, 40 mmol), 2-fluoropyridine (1.3 g, 13 mmol), and N,N-dimethyl formamide (15 mL) was added sodium hydride (1.4 g, 40 mmol, 66% in oil) at 0° C, which was stirred at room temperature for 20 minutes and at 70° C for one hour. To the reaction mixture was added water, and extracted with ethyl acetate. The organic layer was washed with saturated sodium chloride water, and the solvent thereof was evaporated under a reduced pressure. The residue was purified by NH silica gel column chromatography (ethyl acetate:heptane=1:1) to obtain the title compound (1.9 g).

$^1$H-NMR Spectrum (CDCl$_3$) δ (ppm): 4.71 (2H,s), 5.38 (2H,s), 6.81 (1H,td,J=0.9,8.4 Hz), 6.89 (1H,ddd,J=0.9,5.1, 7.1 Hz), 7.37-7.47 (4H,m), 7.59 (1H,ddd,J=2.0,7.1,8.3 Hz), 8.17 (1H,ddd,J=0.7,2.0, 5.1 Hz).

Preparation Example 1-3-2

4-(Pyridin-2-yloxymethyl)-benzaldehyde

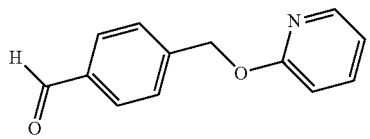

To a mixture of (4-(pyridin-2-yloxymethyl)-phenyl)methanol described in Preparation Example 1-3-1 (1.9 g, 8.6 mmol) and methylene chloride (30 mL) was added manganese dioxide (15 g, 17 mmol) at room temperature, which was stirred overnight at this temperature. The reaction mixture was filtered through a celite bed, and the solvent thereof was evaporated under a reduced pressure. The residue was purified by silica gel column chromatography (ethyl acetate:heptane=1:4) to obtain the title compound (770 mg).

$^1$H-NMR Spectrum (CDCl$_3$) δ (ppm): 5.48 (2H,s), 6.85 (1H,d,J=8.2 Hz), 6.90-6.93 (1H,m), 7.60-7.64 (3H,m), 7.89 (2H,d, J=8.1 Hz), 8.16 (1H,dd,J=1.3,4.9 Hz), 10.0 (1H,s).

Preparation Example 1-3-3

2-(4-((E)-2-nitro-vinyl)-benzyloxy)-pyridine

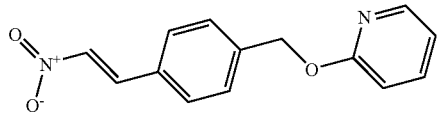

A mixture of 4-(pyridin-2-yloxymethyl)-benzaldehyde described in Preparation Example 1-3-2 (23.4 g, 110 mmol), nitro methane (33.6 g, 550 mmol), ammonium acetate (17.0 g, 220 mmol) and acetic acid (200 mL) was stirred at 100° C for one hour 45 minutes. While the reaction solution was being stirred under ice cooling, small amount of water was added thereto, and the precipitated solids were filtered to obtain title compound (21.0 g).

$^1$H-NMR Spectrum (DMSO-d$_6$) δ (ppm): 5.41 (2H,s), 6.91 (1H,dd,J=0.8,8.4 Hz), 6.99-7.10 (1H,m), 7.53 (2H,d,J=8.0 Hz), 7.72-7.79 (1H,m), 7.86 (2H,d,J=8.0 Hz), 8.13 (1H,d, J=10 Hz), 8.15-8.20 (1H,m), 8.23 (1H,d,J=10 Hz).

Preparation Example 1-3-4

2-(4-(2-Nitro-ethyl)-benzyloxy)-pyridine

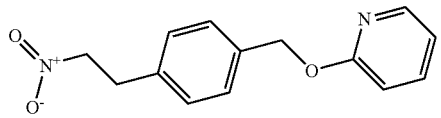

To a solution of 2-(4-((E)-2-nitro-vinyl)-benzyloxy)-pyridine described in Preparation Example 1-3-3 (21.0 g, 81.9 mmol), acetic acid (21 mL) and dimethylsulfoxide (200 mL) was added sodium borohydride (4.96 g, 131 mmol), while being suitably cooled at room temperature. After sodium borohydride was added, the cold bath was removed, the solution was stirred at room temperature for 15 minutes. The reaction solution was partitioned into water and ethyl acetate. The ethyl acetate layer was washed twice with water and once with sodium chloride water, this was dried over anhydrous magnesium sulfate, and the solvent thereof was evaporated under a reduced pressure. The residue was purified by NH silica gel column chromatography (ethyl acetate:heptane=1:3) to obtain the title compound (16.3 g).

$^1$H-NMR Spectrum (DMSO-d$_6$) δ (ppm): 3.23 (2H,t,J=6.8 Hz), 4.85 (2H,t,J=6.8 Hz), 5.32 (2H,s), 6.82-6.88 (1H,m), 6.96-7.01 (1H,m), 7.28 (2H,d,J=8.0 Hz), 7.38 (2H,d,J=8.0 Hz), 7.69-7.74 (1H,m), 8.15-8.19 (1H,m).

Preparation Example 1-3-5

(4-(Pyridin-2-yloxymethl)-phenyl)-acetohydroxymoyl chloride

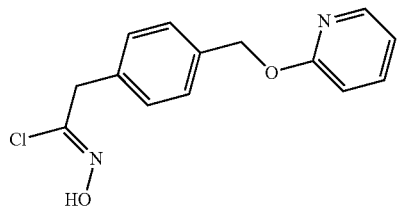

To methanol (75 mL) was added lithium wire (323 mg, 46.6 mmol), and dissolved. To this mixture solution was added 2-(4-(2-nitro-ethyl)-benzyloxy)-pyridine described in Preparation Example 1-3-4 (6.0 g, 23.3 mmol), and the reaction solution was concentrated under a reduced pressure. Toluene was added to the residue, and the solvent thereof was concentrated under a reduced pressure. A solution of the resulting residue in methylene chloride (90 mL) and tetrahydrofuran (45 mL) was cooled to −78° C and titanium (IV) chloride (8.15 mL, 74.4 mmol) was added thereto while stirring. Immediately after adding titanium (IV) chloride, the reaction solution was stirred at 0° C for 10 minutes, and then at room temperature for 30 minutes. The reaction solution was poured over an ice water and extracted with ethyl acetate. The organic layer was dried over anhydrous magnesium sulfate, and magnesium sulfate was removed by filtration. The filtrate was passed through a glass filter lined with neutral silica gel (eluted with ethyl acetate). The resulting eluate was concentrated under a reduced pressure. A small amount of ethyl acetate was added to the residue and the precipitated solids were filtered to obtain the title compound (1.86 g).

$^1$H-NMR Spectrum (DMSO-d$_6$) δ (ppm): 3.82 (2H,s), 5.33 (2H,s), 6.84-6.89 (1H,m), 6.97-7.01 (1H,m), 7.25 (2H,d, J=8.4 Hz), 7.41 (2H,d,J=8.4 Hz), 7.70-7.76 (1H,m), 8.15-8.18 (1H,m), 11.7 (1H,s).

Alternative method to the preparation method for (4-(pyridin-2-yloxymethyl)-phenyl)-acetohydroxymoyl chloride described in [Preparation Example 1-3-5]

Preparation Example 1-4-1

2-(4-Bromo-benzyloxy)-pyridine

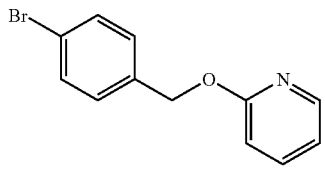

To a solution of 4-bromobenzyl alcohol (25 g, 130 mmol) in N,N-dimethyl formamide (125 mL) was added potassium tert-butoxide (15.8 g, 141 mmol) at room temperature, which was stirred at 54° C. for 10 minutes. To this reaction solution was added 2-fluoropyridine (15 mL, 154 mmol) at from 40° C to 58° C, which was stirred further at 65° C for 30 minutes. The reaction solution was allowed to room temperature, and water and ethyl acetate were added to carry out liquid separation. The aqueous layer was extracted further with ethyl acetate (twice). The ethyl acetate layers were combined, washed with water (three times) and sodium chloride water (once), dried over anhydrous magnesium sulfate and then filtered. The filtrate thereof was concentrated under a reduced pressure. To the residue was added diethyl ether, and concentrated under a reduced pressure to obtain the title compound (34 g) as a crude product.

$^1$H-NMR Spectrum (CDCl3) δ (ppm) 5.33 (2H,s), 6.87-6.70 (1H,m), 6.98-7.02 (1H,m), 7.38-7.44 (2H,m), 7.55-7.60 (2H,m), 7.71-7.76 (1H,m), 8.15-8.18 (1H,m).

Preparation Example 1-4-2

4-(Pyridin-2-yloxymethyl)-benzaldehyde

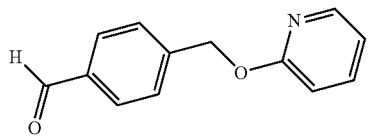

To a tetrahydrofuran solution (120 mL) of 2-(4-bromobenzyloxy)-pyridine described in Preparation Example 1-4-1 (34 g, 128 mmol) was added n-butyl lithium (50 mL, 2.6M hexane solution, 134 mmol) dropwise at −78° C. After stirring for 30 minutes, to this reaction solution was added N,N-dimethylformamide (10 mL, 134 mmol) dropwise at −78° C, which was stirred at room temperature. To the reaction solution were added water and ethyl acetate to carry out liquid separation. The ethyl acetate layer was washed with water (twice) and sodium chloride water (once). The aqueous layers were combined and extracted with ethyl acetate. The resulting ethyl acetate layer was washed with water (twice) and sodium chloride water (once). The ethyl acetate layer obtained earlier and the ethyl acetate layer obtained this time were combined, dried over anhydrous magnesium sulfate and then filtered. The filtrate thereof was concentrated under a reduced pressure to obtain the title compound (26.8 g) as a crude product.

Preparation Example 1-4-3

2-(4-((E)-2-nitro-vinyl)-benzyloxy)-pyridine

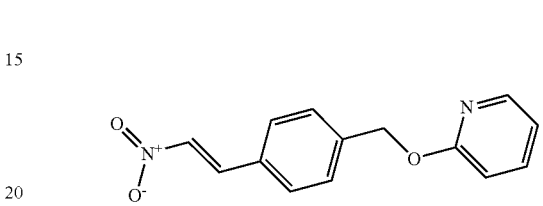

A mixture of 4-(pyridin-2-yloxymethyl)-benzaldehyde described in Preparation Example 1-4-2 (26.8 g, 126 mmol), nitro methane (34 mL, 630 mmol), ammonium acetate (19 g, 252 mmol) and acetic acid (90 mL) was stirred at 100° C for 90 minutes. To the reaction solution were added ethyl acetate and water to carry out liquid separation. The organic layer thereof was separated, washed with water (five times) and saturated sodium bicarbonate water (once), dried over anhydrous magnesium sulfate and then filtered. The filtrate thereof was concentrated under a reduced pressure to obtain the title compound (31 g) as a crude product.

Preparation Example 1-4-4

2-(4-(2-Nitro-ethyl)-benzyloxy)-pyridine

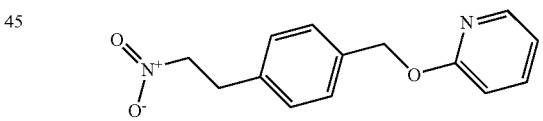

To a solution of 2-(4-((E)-2-nitro-vinyl)-benzyloxy)-pyridine described in Preparation Example 1-4-3 (30.8 g, 120 mmol) and acetic acid (7.4 mL) in dimethylsulfoxide (150 mL) was added sodium borohydride (2.45 g, 64.8 mmol) at below 30° C. The reaction solution was stirred at room temperature for 40 minutes. To the reaction solution were added water and ethyl acetate and diethyl ether at below 30° C, and partitioned into water and organic layer. The aqueous layer was extracted with ethyl acetate. The organic layer and ethyl acetate layer were combined, washed with water (3 times) and sodium chloride water (once), dried over anhydrous magnesium sulfate and then filtered. The filtrate thereof was concentrated under a reduced pressure. The residue was purified by NH silica gel column chromatography (ethyl acetate:heptane=1:4) to obtain the title compound (15.2 g).

Preparation Example 1-4-5

(4-(Pyridin-2-yloxymethyl)-phenyl)-acetohydroxymoyl chloride

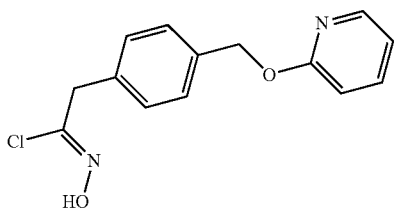

To a solution of 2-(4-(2-nitro-ethyl)-benzyloxy)-pyridine described in Preparation Example 1-4-4 (15.2 g, 59 mmol) in methanol (80 mL) was added lithium methoxide (4.49 g, 118 mmol), which was stirred for 3 minutes. The reaction solution was concentrated under a reduced pressure. To the residue was added toluene, and the solvent thereof was concentrated under a reduced pressure. A solution of the resulting residue in methylene chloride (100 mL) and tetrahydrofuran (50 mL) was cooled to −66° C, and titanium (IV) chloride (20.8 mL, 189 mmol) was added thereto while stirring. The reaction solution was stirred at 0° C. for 10 minutes, and then stirred at room temperature for 30 minutes. The reaction solution was poured over an ice water, and stirred at room temperature for 30 minutes. To the reaction solution were added ethyl acetate and diethyl ether to carry out liquid separation. The organic layer was washed with water (3 times) and sodium chloride water (once). The aqueous layers were combined, and extracted with ethyl acetate (twice). The ethyl acetate layers were combined and washed with water (3 times) and sodium chloride water (once). The organic layer and ethyl acetate layer were combined, dried over anhydrous magnesium sulfate and sodium sulfate and then filtered. The filtrate thereof was concentrated under a reduced pressure to obtain the title compound (11.5 g) as a raw product.

Reference Example 2

3-(3-(4-(Pyridin-2-yloxymethyl)-benzyl)-isoxazol-5-yl)-pyridin-2-ylamine (Alternative Method)

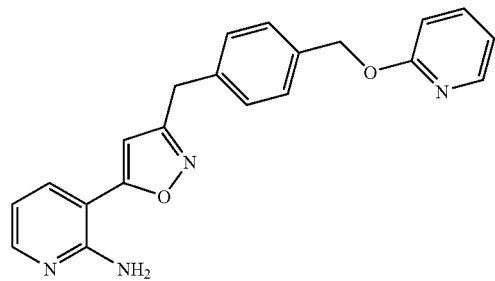

To a mixture of zinc chloride (8.82 g) and tetrahydrofuran (130 mL) was added 3-ethinyl-pyridin-2-yl amine described in Preparation Example 1-1-5 (3 g, purity 98%) and (4-(pyridin-2-yloxymethyl)-phenyl)-acetohydroxymoyl chloride described in Preparation Example 1-3-5 (17.4 g, purity 94%) at 0° C. The reaction mixture was allowed to room temperature and, while the internal temperature was being maintained at below 28° C using a water bath, triethylamine (9.02 mL) was added thereto dropwise. The reaction mixture was stirred at room temperature for 20 minutes, and then was stirred for one hour at 35° C. The reaction mixture was allowed to room temperature, to the reaction mixture was added an aqueous ammonium chloride and ethyl acetate, an aqueous ammonia was added to become a pH value to be approximately 8, and then extracted. The organic layer was washed with saturated sodium chloride water, this was dried over anhydrous magnesium sulfate, and the solvent thereof was evaporated under a reduced pressure. The residue was purified by NH silica gel column chromatography (heptane:ethyl acetate=3:2), and then crystallized using a mixed solvent of tert-butyl methyl ether and heptane to obtain the title compound (5.32 g).

4-(pyridin-2-yloxymethyl)-phenyl-acetohydrxymoyl chloride described in Preparation Example 1-3-5 and Preparation Example 1-4-5 can also be prepared according to the alternative method described below.

Preparation Example 2-1-1

Methyl 3-(4-(pyridin-2-yloxymethyl)-phenyl)-oxiran-2-carboxylate

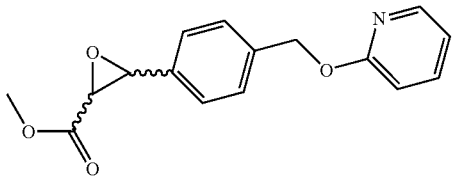

To a mixture of 4-(pyridin-2-yloxymethyl)-benzaldehyde described in Preparation Example 1-3-2 (24.8 g) and tetrahydrofuran (160 mL) was added methyl chloroacetate (10.2 mL) at −15° C, and sodium methoxide (23.7 mL, 28% methanol solution) was then added thereto at the same temperature. The reaction mixture was stirred at 0° C for one hour, and then was stirred for two hours at room temperature. The reaction mixture was added to ice water (800 mL) containing acetic acid (6 mL), and the reaction mixture was allowed to room temperature. To the reaction mixture was added ethyl acetate, and extracted, then, the organic layer was separated, washed with saturated sodium chloride water, and dried over anhydrous magnesium sulfate. The solvent thereof was evaporated under a reduced pressure to obtain the title compound (30.2 g).

$^1$H-NMR Spectrum (CDCl$_3$) δ (ppm): 3.51 (1H,d,J=1.8 Hz), 3.83 (3H,s), 4.11 (1H,d,J=1.8 Hz), 5.38 (2H,s), 6.81 (1H,td,J=0.9,8.4 Hz), 6.89 (1H,ddd,J=0.9,5.1,7.1 Hz), 7.29-

$^1$H-NMR Spectrum (CDCl$_3$) δ (ppm): 3.81 (2H,s), 5.36 (2H,s), 6.81 (1H,d,J=8.2 Hz), 6.88-6.91 (1H,m), 7.28 (2H,d, J=8.1), 7.43 (2H,d,J=8.1 Hz), 7.57-7.62 (1H,m), 8.17-8.19 (1H,m).

7.31 (2H,m), 7.47 (2H,d,J=8.2 Hz), 7.59 (1H,ddd, J=2.0,7.1, 8.4 Hz), 8.17 (1H,ddd,J=0.8,2.0,5.1 Hz).

Preparation Example 2-1-2

Sodium 3-(4-(pyridin-2-yloxymethyl)-phenyl)-oxiran-2-carboxylte

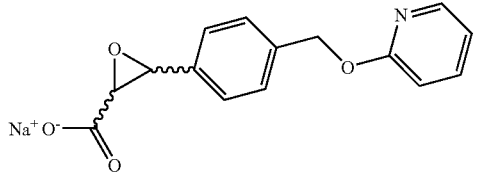

To a mixture of methyl 3-(4-(pyridin-2-yloxymethyl)-phenyl)-oxiran-2-carboxylate described in Preparation Example 2-1-1 (19.9 g) and ethanol (300 mL) were sequentially added sodium methoxide (14.2 mL, 28% methanol solution), water (1.3 mL), tetrahydrofuran (100 mL) at 0° C, which was stirred at room temperature for one hour. To the reaction mixture was added diethyl ether (200 mL), and the precipitated solids were filtered to obtain the title compound (14.3 g).

$^1$H-NMR Spectrum (CD$_3$OD) δ (ppm): 3.31 (1H,d,J=1.8 Hz), 3.88 (1H,d,J=1.8 Hz), 5.33 (2H,s), 6.84 (1H,td,J=0.9,8.2 Hz), 6.94 (1H,ddd,J=0.9,5.1,7.1 Hz), 7.29-7.31 (2H,m), 7.42 (2H,d,J=8.2 Hz), 7.68 (1H,ddd,J=2.0,7.1,8.4 Hz), 8.12 (1H, ddd,J=0.7,2.0,5.1 Hz).

Preparation Example 2-1-3

(4-(Pyridin-2-yloxymethyl)-phenyl)-acetaldehyde

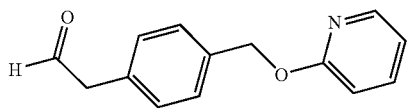

A mixture of sodium 3-(4-(pyridin-2-yloxymethyl)-phenyl)-oxiran-2-carboxylate described in Preparation Example 2-1-2 (9.95 g), toluene (200 mL), water (120 mL) and acetic acid (16 mL) was stirred at 73° C for 90 minutes. The reaction mixture was allowed to room temperature, to the reaction mixture was added ethyl acetate, and extracted, and then the organic layer was separated, washed with saturated sodium chloride water, and dried over anhydrous magnesium sulfate. The solvent thereof was evaporated under a reduced pressure to obtain the title compound (6.82 g).

$^1$H-NMR Spectrum (CDCl$_3$) δ (ppm): 3.70 (2H,d,J=2.2 Hz), 5.38 (2H,s), 6.81 (1H,td,J=0.8,8.2 Hz), 6.89 (1H,ddd, J=0.9,5.1,7.1 Hz), 7.24 (2H,d,J=8.1), 7.48 (2H,d,J=8.1 Hz), 7.59 (1H,ddd,J=2.0,7.1,8.4 Hz), 8.18 (1H,ddd,J=0.6,2.0,5.0 Hz), 9.75 (1H,t,J=2.4).

Preparation Example 2-1-4

(4-(Pyridin-2-yloxymethyl)-phenyl)-acetaldehyde oxime (E/Z mixture)

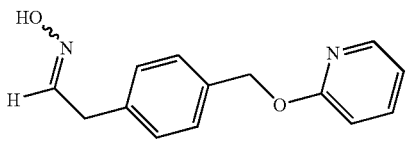

To a mixture of hydroxylamine sulfate (19.7 g) and water (250 mL) was added an aqueous solution of 1N sodium hydroxide (240 mL) at 0° C, which was stirred at the same temperature for 15 minutes. Then, at the same temperature, to the reaction mixture was added a mixture of (4-(pyridin-2-yloxymethyl)-phenyl)-acetaldehyde described in Preparation Example 2-1-3 (27.3 g) and methanol (250 mL) dropwise, which was stirred overnight at room temperature. The precipitated solids were filtered to obtain the title compound (20.3 g) as a mixture of E isomer and Z isomer.

$^1$H-NMR Spectrum (CDCl$_3$) δ (ppm): 3.54 (2H,d,J=6.2 Hz), 3.74 (2H,d,J=5.3 Hz), 5.36 (2H+2H,s), 6.79-6.81 (1H+ 1H,m), 6.87-6.90 (1H+2H,m), 7.22-7.24 (2H+2H,m), 7.42-7.44 (2H+2H,m), 7.53 (1H,t,J=6.3 Hz), 7.56-7.61 (1H+1H, m), 8.17-8.18 (1H+1H, m) (underbar=E or Z).

Preparation Example 2-1-5

(4-(Pyridin-2-yloxymethyl)-phenyl)-acetohydroxymoyl chloride

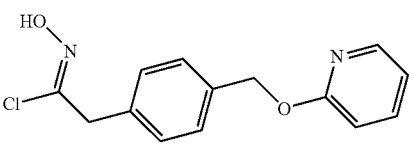

To a mixture of (4-(pyridin-2-yloxymethyl)-phenyl)-acetaldehyde oxime (E/Z mixture) described in Preparation Example 2-1-4 (132 mg) and N,N-dimethyl formamide (2 mL) was added N-chlorosuccinimide (72.8 mg) at room temperature. Then, at the same temperature, hydrochloric acid gas was blown into the reaction mixture and stirred at the same temperature for 90 minutes. To the reaction mixture was added ethyl acetate and water and extracted, then the organic layer was separated, washed with saturated sodium chloride water, and dried over anhydrous magnesium sulfate. The solvent thereof was evaporated under a reduced pressure, the resulting residue was washed with a mixed solvent of diethyl ether and heptane to obtain the title compound (123 mg).

Reference Example 3

3-(3-(4-(Pyridin-2-yloxymethyl)-benzyl)-isoxazol-5-yl)-pyridin-2-yl amine (Alternative Method)

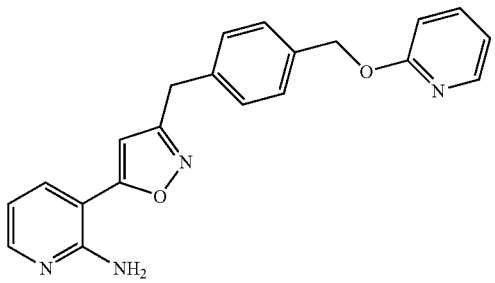

To a solution of di-tert-butyl(3-(3-(4-((pyridin-2-yloxy)methyl)benzyl)isoxazol-5-yl)pyridin-2-yl)imidodicarbonate described in Preparation Example 3-1-2 (11.8 g, purity approximately 70%) and dichloromethane (120 mL) was added trifluoroacetic acid (40 mL) at 0° C. Stirring was carried out at room temperature for 14 hours. To the reaction solution was added saturated sodium bicarbonate water at 20° C or lower, extracted with ethyl acetate, and then purified by NH-silica gel column chromatography (heptane:ethyl acetate=1:1). The solvent was concentrated under a reduced pressure, tert-butyl methyl ether was added to the resulting residue, and solids were filtered to obtain the title compound (7.29 g).

$^1$H-NMR Spectrum (DMSO-d6) δ (ppm): 4.04 (2H,s), 5.32 (2H,s), 6.26 (2H,brs), 6.69 (1H,dd,J=4.8,8.0 Hz), 6.81 (1H,s), 6.83-6.87 (1H,m), 6.97-7.00 (1H,m), 7.33 (2H,d,J=8.0 Hz), 7.40 (2H,d,J=8.0 Hz), 7.69-7.74 (1H,m), 7.87 (1H,dd,J=2.0, 7.6 Hz), 8.08 (1H,dd,J=2.0,7.6 Hz), 8.15-8.17 (1H,m).

The starting material, di-tert-butyl(3-(3-(4-((pyridin-2-yloxy)methyl)benzyl)isoxazol-5-yl)pyridin-2-yl)imidodicarbonate, was synthesized according to the following methods.

Preparation Example 3-1-1

Di-tert-butyl(3-ethinyl pyridin-2-yl)imidodicarbonate

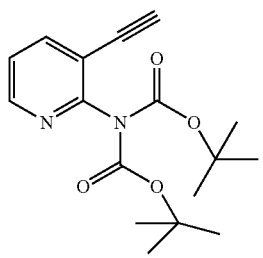

3-Ethinyl-pyridin-2-ylamine described in Preparation Example 1-1-5 (6.34 g), di-tert-butyl dicarbonate (58.5 g), triethylamine (27.1 g), 4-dimethylaminopyridine (655 mg), and tetrahydrofuran (254 mL) were stirred at room temperature for 18 hours. Silica gel was added to the reaction solution, and the solvent was concentrated under a reduced pressure. The resulting residue was purified by silica gel column chromatography (heptane:ethyl acetate=3:1) to obtain the title compound (15 g).

$^1$H-NMR Spectrum (DMSO-d6) δ (ppm): 1.32 (18H,s), 4.59 (1H,s), 7.39-7.44 (1H,m), 7.99-8.03 (1H,m), 8.46-8.48 (1H,m).

Preparation Example 3-1-2

Di-tert-butyl(3-(3-(4-((pyridin-2-yloxy) methyl)benzyl)isoxazol-5-yl)pyridin-2-yl)imidodicarbonate

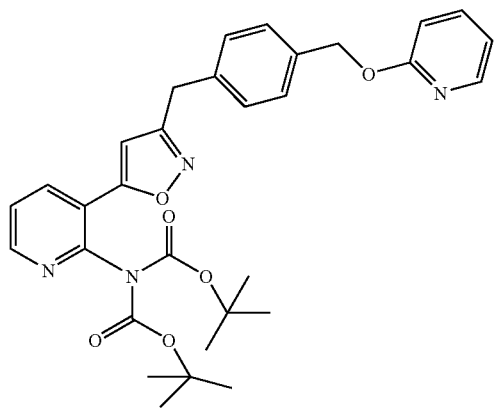

Under stirring at room temperature, to a solution of di-tert-butyl(3-ethinyl pyridin-2-yl)imidodicarbonate described in Preparation Example 3-1-1 (12 g), 2-(4-(2-nitro-ethyl)-benzyloxy)pyridine described in Preparation Example 1-3-4 (19.4 g), 4-dimethyl aminopyridine (230 mg), tetrahydrofuran (200 mL) was added di-tert-butyl dicarbonate (28.8 g) divided into four portions over 8 hours. After the additions were finished, stirring was carried out at room temperature for an additional 22 hours. Silica gel was added to the reaction solution and the solvent was concentrated under a reduced pressure. The resulting residue was purified by silica gel column chromatography (heptane:ethyl acetate=3:1 then 2:1) to obtain the title compound (11.8 g, containing approximately 70% of the target compound).

Preparation Example 3-2-1

Di-tert-butyl(3-(3-(4-((pyridin-2-yloxy)methyl)benzyl)isoxazol-5-yl)pyridin-2-yl)imidodicarbonate (Alternative Method 1)

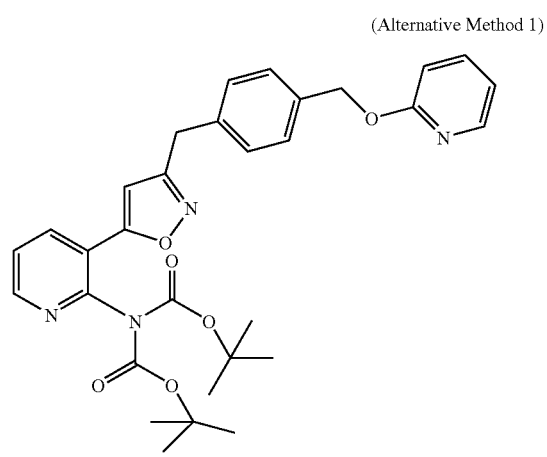

Under stirring at 50° C, to a solution of di-tert-butyl(3-ethinyl pyridin-2-yl)imidodicarbonate described in Preparation Example 3-1-1 (2.0 g), 2-(4-(2-nitro-ethyl)-benzyloxy)pyridine described in Preparation Example 1-3-4 (2.44 g), triethylamine (0.086 uL) and tetrahydrofuran (20 mL) was added phenyl isocyanate (2.8 mL) divided into four portions over 5.5 hours. After the additions were finished, stirring was carried out at 50° C for another two hours. NH-silica gel was added to the reaction solution, and the solvent was concentrated under a reduced pressure. The resulting residue was purified by NH-silica gel column chromatography (heptane:ethyl acetate=3:1). The resulting solution was concentrated under a reduced pressure and purified by silica gel chromatography (heptane:ethyl acetate=3:1 then 2:1) to obtain the title compound (2.2 g).

$^1$H-NMR Spectrum (DMSO-d6) δ (ppm): 1.18 (18H,s), 4.07 (2H,s), 5.32 (2H,s), 6.58 (1H,s), 6.83-6.86 (1H,m), 6.96-7.01 (1H,m), 7.29 (2H,d,J=8.0 Hz), 7.40 (2H,d,J=8.0 Hz), 7.58 (1H,dd,J=4.8,7.6 Hz), 7.69-7.74 (1H,m), 8.15-8.18 (1H,m), 8.34 (1H,dd,J=2.0,7.6 Hz), 8.59 (1H,dd,J=2.0,5.2 Hz).

Preparation Example 3-3-1

4-Methylene-2-oxo-4H-pyrido[2,3-d][1,3]oxazine-1-carboxylic acid tert-butyl ester

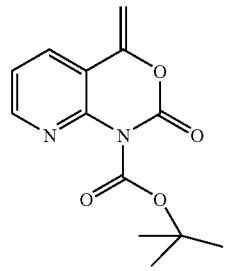

1-(2-Amino-pyridin-3-yl)-ethanone (990 mg), di-tert-butyl dicarbonate (7.92 g), 4-dimethylaminopyridine (88.8 mg), triethylamine (4.95 mL) and tetrahydrofuran (16.5 mL) were stirred at room temperature for 24 hours. Silica gel was added to the reaction solution and the solvent was concentrated under a reduced pressure. The resulting residue was purified by silica gel column chromatography (heptane:ethyl acetate=2:1) to obtain the title compound (1.48 g).

$^1$H-NMR Spectrum (DMSO-d6) δ (ppm): 1.56 (9H,s), 5.01 (1H,d,J=3.6 Hz), 5.45 (1H,d,J=3.6 Hz), 7.28 (1H,dd,J=4.8, 8.0 Hz), 8.25 (1H,dd,J=1.6,8.0 Hz), 8.36 (1H,dd,J=1.6,4.8 Hz).

Preparation Example 3-3-2

Di-tert-butyl(3-(3-(4-((pyridin-2-yloxy)methyl)benzyl)isoxazol-5-yl)pyridin-2-yl)imidodicarbonate (Alternative Method 2)

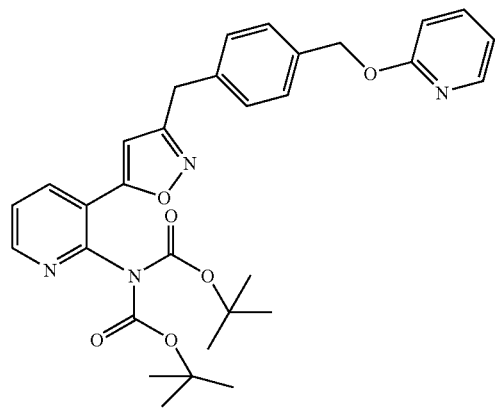

4-Methylene-2-oxo-4H-pyrido[2,3-d][1,3]oxazine-1-carboxylic acid tert-butyl ester described in Preparation Example 3-3-1 (1.48 g), 2-(4-(2-nitro-ethyl)-benzyloxy)pyridine described in Preparation Example 1-3-4 (2.9 g), di-tert-butyl dicarbonate (6.14 g), 4-dimethyl aminopyridine (68.6 mg), and tetrahydrofuran (5 mL) were stirred at room temperature for two hours. Silica gel was added to the reaction solution and the solvent was concentrated under a reduced pressure. The resulting residue was purified by silica gel column chromatography (heptane:ethyl acetate=3:1 then 1:1 then 1:2) to obtain the title compound (2.1 g).

Reference Example 4

3-(3-(4-(Pyridin-2-yloxymethyl)-benzyl)-isoxazol-5-yl)-pyridin-2-ylamine (Alternative Method)

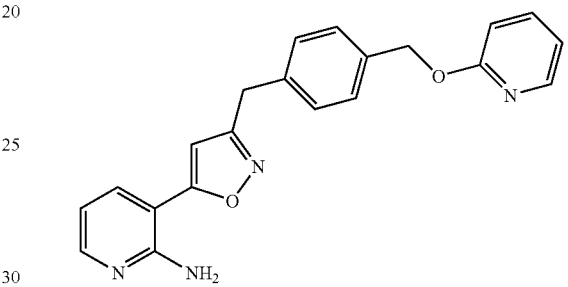

Under a nitrogen atmosphere, a mixture of 2-(4-(5-iodo-isoxazol-3-yl methyl)-benzyloxy)-pyridine described in Preparation Example 4-2-2 (200 mg), 2-N-t-butoxycarbonyl-3-pyridine boric acid described in Preparation Example 4-1-2 (134 mg), sodium carbonate (82 mg), tetrakis(triphenyl phosphine) palladium (0) (59 mg), 1,2-dimethoxyethane (6 mL) and water (1 mL) was stirred at 80° C for two hours. This mixture was cooled to room temperature, and ethyl acetate and water were added thereto. The organic layer thereof was separated, washed with water and saturated sodium chloride water, dried over anhydrous magnesium sulfate and then filtered. The filtrate thereof was adsorbed onto silica gel, then, purified by silica gel column chromatography (heptane:ethyl acetate=4:1 to 1:1 to ethyl acetate) to obtain the title compound (116 mg).

The starting material, 2-N-t-butoxycarbonyl-3-pyridine boric acid, was synthesized according to the following methods.

Preparation Example 4-1-1

Pyridin-2-yl-carbamic acid tert-butyl ester

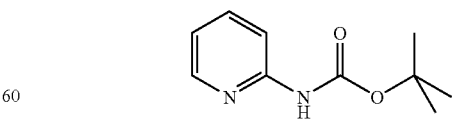

To a solution of tert-butyl alcohol (650 mL) and di-tert-butyl carbonate (24 g) was added 2-Aminopyridine (9.4 g) slowly. This mixture was stirred at room temperature for 24 hours. This reaction solution was concentrated under a reduced pressure, and the residue thereof was purified by silica gel column chromatography (heptane:ethyl acetate=1:1) to obtain the title compound (18 g).

$^1$H-NMR Spectrum (DMSO-d$_6$) δ (ppm): 1.47 (9H,s), 6.99-7.03 (1H,m), 7.70-7.74 (1H,m), 7.77-7.80 (1H,m), 8.23-8.24 (1H,m), 9.72 (1H,brs).

Preparation Example 4-1-2

2-N-t-butoxy carbonyl-3-pyridine boric acid

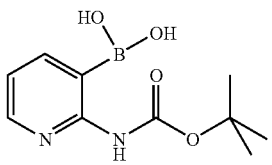

A solution of pyridin-2-yl-carbamic acid tert-butyl ester described in Preparation Example 4-1-1 (16 g) and N,N,N',N'-tetramethyl ethylenediamine (25 g) in tetrahydrofuran (400 mL) was cooled to −70° C, n-butyl lithium (78 mL, 2.64M heptane solution) was then added thereto dropwise over one hour, and stirred for 10 minutes. This mixture was heated to between −10° C. and −6° C, and stirred at this temperature for two hours. Again, this solution was cooled to 70° C, and triisobutyl borate (58 g) was added thereto dropwise over one hour. This mixture was heated to 0° C, then, a saturated aqueous ammonium chloride was added thereto. To the produced yellow solid was added ether, and stirred, and then, a solid was recovered by filtration and washed with ether and water. This solid was in vacuo to obtain the title compound (14 g).

$^1$H-NMR Spectrum (DMSO-d$_6$) δ (ppm): 1.32-1.41 (9H, m), 6.80-6.84 (1H,m), 7.95-7.8.13 (2H,m).

The starting material, 2-(4-(5-iodo-isoxazol-3-yl methyl)-benzyloxy)-pyridine, was synthesized according to the following methods.

Preparation Example 4-2-1

2-(4-(5-Tributylstannyl-isoxazol-3-yl methyl)-benzyloxy)-pyridine

To a solution of tri-N-butyl ethinyl tin (3 g), 2-(4-(2-nitroethyl)-benzyloxy)-pyridine (4.9 g) and 4-dimethyl aminopyridine (116 mg) in tetrahydrofuran (90 mL) was added a solution of di-tert-butyldicarbonate (7.3 g) in tetrahydrofuran (30 mL), which was stirred at room temperature for 15 hours. Ethyl acetate and water were added to this mixture. The organic layer thereof was separated, washed with water and saturated sodium chloride water, dried over anhydrous magnesium sulfate and then filtered. The filtrate thereof was adsorbed to silica gel, then, purified by silica gel column chromatography (heptane:ethyl acetate=4:1) to obtain the title compound (5.3 g).

$^1$H-NMR Spectrum (DMSO-d$_6$) δ (ppm): 0.81-0.85 (9H, m), 1.08-1.12 (6H,m), 1.23-1.30 (6H,m), 1.46-1.54 (6H,m), 4.00 (2H,s), 5.30 (2H,s), 6.40 (1H,s), 6.83-6.86 (1H,m), 6.97-7.00 (1H,m), 7.25-7.26 (2H,m), 7.36-7.38 (2H,m), 7.69-7.74 (1H,m), 8.15-8.17 (1H,m).

Preparation Example 4-2-2

2-(4-(5-Iodo-isoxazol-3-yl methyl)-benzyloxy)-pyridine

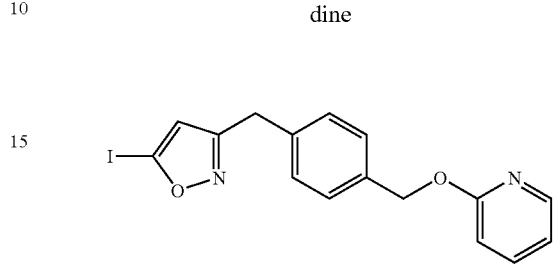

To a solution of 2-(4-(5-tributylstannyl-isoxazol-3-yl methyl)-benzyloxy)-pyridine (5.1 g) in tetrahydrofuran (15 mL) was added iodine (2.5 g) at 0° C. This mixture was stirred for 20 minutes at this temperature. To this mixture was added an aqueous solution of 10% sodium thiosulfate and ethyl acetate. The organic layer thereof was separated, washed with saturated sodium chloride water, dried over anhydrous magnesium sulfate and then filtered. The filtrate thereof was concentrated, and the residue thereof was purified by silica gel column chromatography (heptane:ethyl acetate=10:1 to 4:1) to obtain the title compound (2.4 g).

$^1$H-NMR Spectrum (DMSO-d$_6$) δ (ppm): 3.99 (2H,s), 5.31 (2H,s), 6.66 (1H,s), 6.84-6.87 (1H,m), 6.97-7.00 (1H, nm), 7.26 (2H,d,J=8 Hz), 7.39 (2H,d,J=8 Hz), 7.70-7.74 (1H,m), 8.16-8.17 (1H,m).

Example 1

3-(3-(4-(Pyridin-2-yloxymethyl)-benzyl)-isoxazol-5-yl)-pyridin-2-ylamine hydrochloride To a suspension of 3-(3-(4-(pyridin-2-yloxymethyl)-benzyl)-isoxazol-5-yl)-pyridin-2-ylamine (500 mg) in methanol (2 mL) was added concentrated hydrochloric acid (123 µL) dropwise at 25° C, and the suspension turned into a solution. After adding tert-butyl methyl ether (2 mL) dropwise for 20 minutes at the same temperature and seeding, crystals precipitated. After stirring at 25° C for 10 minutes, tert-butyl methyl ether (6 mL) was added dropwise for 30 minutes, and the mixture was stirred at the same temperature for two hours. The precipitated crystals were filtered and dried to obtain the title compound (513 mg) as a white crystal.

$^1$H-NMR Spectrum (DMSO-d$_6$) δ (ppm): 4.06 (2H,s), 5.30 (2H,s), 6.82-6.86 (1H,m), 6.95-7.00 (3H,m), 7.32 (2H,d, J=8.0 Hz), 7.40 (2H,d,J=8.0 Hz), 7.66-7.97 (2H,m), 8.13-8.18 (2H,m), 8.29 (1H,dd,J=1.6,7.6 Hz).

Example 2

3-(3-(4-(Pyridin-2-yloxymethyl)-benzyl)-isoxazol-5-yl)-pyridin-2-ylamine dihydrochloride 3-(3-(4-(Pyridin-2-yloxymethyl)-benzyl)-isoxazol-5-yl)-pyridin-2-yl amine (1 g) was dissolved in methanol (50 mL), and concentrated hydrochloric acid (1.18 mL) was added thereto at room temperature. This mixed solution was stirred at room temperature for 5 minutes, and then concentrated under a reduced pressure. To the residue were added ethanol and tert-butyl methyl ether, and subjected to ultrasound treatment. The precipitated solids were filtered, washed with tert-butyl methyl ether and dried in vacuo to obtain the title compound (908 mg).

$^1$H-NMR Spectrum (DMSO-d$_6$) δ (ppm): 4.09 (2H,s), 5.33 (2H,s), 6.87 (1H,d,J=8.4 Hz), 6.98-7.06 (3H,m), 7.34 (2H,d, J=8.0 Hz), 7.42 (2H,d,J=8.0 Hz), 7.71-7.75 (1H,m), 8.10 (1H,brs), 8.16-8.18 (1H,m), 8.20 (1H,dd,J=1.6,6.0 Hz), 8.38 (1H,dd,J=1.6,7.6 Hz).

Example 3

3-(3-(4-(Pyridin-2-yloxymethyl)-benzyl)-isoxazol-5-yl)-pyridin-2-ylamine hydrobromide 3-(3-(4-(Pyridin-2-yloxymethyl)-benzyl)-isoxazol-5-yl)-pyridin-2-yl amine (200 mg) was dissolved in methanol and ethyl acetate, and an aqueous solution of hydrobromic acid (1.16N, 0.45 mL) was added thereto. The solvent was concentrated under a reduced pressure. To the residue was added toluene, and concentrated under a reduced pressure. To the residue were added ethanol and tert-butyl methyl ether, then subjected to ultrasound treatment to be solidified. The solids were filtered to obtain the title compound (210 mg).

$^1$H-NMR Spectrum (DMSO-d$_6$) δ (ppm): 4.08 (2H,s), 5.33 (2H,s), 6.84 (1H,d,J=8.0 Hz), 6.95-7.02 (3H,m), 7.33 (2H,d, J=8.0 Hz), 7.42 (2H,d,J=8.0 Hz), 7.70-7.75 (1H,m), 8.14 (1H,dd,J=1.6,5.6 Hz), 8.15-8.18 (1H,m), 8.28 (1H,dd,J=1.6, 7.6 Hz).

Example 4

3-(3-(4-(Pyridin-2-yloxymethyl)-benzyl)-isoxazol-5-yl)-pyridin-2-ylamine dihydrobromide 3-(3-(4-(Pyridin-2-yloxymethyl)-benzyl)-isoxazol-5-yl)-pyridin-2-yl amine (200 mg) was dissolved in methanol and ethyl acetate, and an aqueous solution of hydrobromic acid (1.16N,0.90 mL) was added thereto. The solvent was concentrated under a reduced pressure. To the residue was added toluene, and concentrated under a reduced pressure. To the residue was added ethanol, and concentrated under a reduced pressure. To the residue was added a small amount of ethanol, then subjected to ultrasound treatment to be solidified. The solids were filtered to obtain the title compound (255 mg).

$^1$H-NMR Spectrum (DMSO-d$_6$) δ (ppm): 4.10 (2H,s), 5.33 (2H,s), 6.87 (1H,dd,J=0.8,8.0 Hz), 6.98-7.08 (3H,m), 7.34 (2H,d,J=8.0 Hz), 7.42 (2H,d,J=8.0 Hz), 7.72-7.77 (1H,m), 8.16-8.19 (2H,m), 8.39 (1H,dd,J=1.2,7.6 Hz).

Example 5

3-(3-(4-(Pyridin-2-yloxymethyl)-benzyl)-isoxazol-5-yl)-pyridin-2-yl amine phosphate 3-(3-(4-(Pyridin-2-yloxymethyl)-benzyl)-isoxazol-5-yl)-pyridin-2-yl amine (65 mg) was dissolved in methanol (0.87 mL) and ethyl acetate (0.87 mL), and phosphoric acid (85%, 0.013 mL) was added thereto. The solvent was concentrated under a reduced pressure, to the residue was added ethanol (4.3 mL), and dissolved by heating. Then, after filtration, the solution was left at room temperature to be solidified. The solids were filtered to obtain the title compound (31 mg).

$^1$H-NMR Spectrum (DMSO-d$_6$) δ (ppm): 4.02 (2H,s), 5.30 (2H,s), 6.26 (2H,brs), 6.67 (1H,dd,J=4.8,7.6 Hz), 6.79 (1H,s), 6.83 (1H,d,J=8.0 Hz), 6.94-6.99 (1H,m), 7.31 (2H,d,J=8.0 Hz), 7.38 (2H,d,J=8.0 Hz), 7.66-7.72 (1H,m), 7.85 (1H,dd, J=2.0,8.0 Hz), 8.07 (1H,d,J=4.8 Hz), 8.14 (1H,dd,J=0.8,4.8 Hz).

Example 6

3-(3-(4-(Pyridin-2-yloxymethyl)-benzyl)-isoxazol-5-yl)-pyridin-2-ylamine hemisulfate To 3-(3-(4-(pyridin-2-yloxymethyl)-benzyl)-isoxazol-5-yl)-pyridin-2-ylamine (1 g) was added methanol (4 mL). While heating and stirring at 40° C, to this suspension was added a solution of concentrated sulfuric acid (79.4 μL) in methanol (1 mL) dropwise, which turned into a solution. After stirring at 40° C for 10 minutes and seeding, crystals precipitated. After stirring at 40° C for 20 minutes, tert-butyl methyl ether (25 mL) was added dropwise at the same temperature for one hour, followed by slow cooling, then stirring at 23° C for three hours. The precipitated crystals were filtered and dried to obtain the title compound (1.04 g).

$^1$H-NMR Spectrum (DMSO-d$_6$) δ (ppm): 4.04 (2H,s), 5.30 (2H,s), 6.81-6.86 (2H, m), 6.88 (1H,d,J=8.0 Hz), 6.88-7.12 (2H,m), 7.31 (2H,d,J=8.0 Hz), 7.39 (2H,d,J=8.0 Hz), 7.67-7.73 (1H,m), 8.05-8.11 (2H,m), 8.13-8.17 (1H,m).

Example 7

3-(3-(4-(Pyridin-2-yloxymethyl)-benzyl)-isoxazol-5-yl)-pyridin-2-ylamine disulfate 3-(3-(4-(Pyridin-2-yloxymethyl)-benzyl)-isoxazol-5-yl)-pyridin-2-yl amine (150 mg) was dissolved in methanol (2 mL) and ethyl acetate (2 mL), and concentrated sulfuric acid (0.026 mL) was added thereto. The solvent was concentrated under a reduced pressure, to the residue was added ethanol (10 mL), and dissolved by heating. Then, the solution was cooled to 0° C, concentrated sulfuric acid (0.026 mL) was added to be solidified. The solids were filtered to obtain the title compound (47 mg).

$^1$H-NMR Spectrum (DMSO-d$_6$) δ (ppm): 4.07 (2H,s), 5.32 (2H,s), 6.88 (1H,d,J=8.0 Hz), 6.98-7.07 (3H,m), 7.32 (2H,d, J=8.0 Hz), 7.40 (2H,d,J=8.0 Hz), 7.72-7.78 (1H,m), 8.04 (2H,brs), 8.12-8.19 (2H,m), 8.37 (1H,dd,J=1.6,8.0 Hz).

Example 8

3-(3-(4-(Pyridin-2-yloxymethyl)-benzyl)-isoxazol-5-yl)-pyridin-2-yl amine methanesulfonate To 3-(3-(4-(pyridin-2-yloxymethyl)-benzyl)-isoxazol-5-yl)-pyridin-2-yl amine (500 mg) was added methanol (1.5 mL), and under heat-stirring at 40° C, to this suspension was added a solution of methanesulfonic acid (96.5 μL) in methanol (0.5 mL) dropwise, which turned into a solution. After stirring at 40° C for 10 minutes and seeding, crystals precipitated. After stirring at 40° C for 20 minutes, tert-butyl methyl ether (10 mL) was added thereto dropwise at the same temperature over one hour, then, after slow cooling, stirring was carried out at 23° C for 15 minutes. The precipitated crystals were filtered and dried to obtain the title compound (629 mg) as a slightly yellow crystal.

$^1$H-NMR Spectrum (DMSO-d$_6$) δ (ppm): 2.32 (3H,s), 4.06 (2H,s), 5.30 (2H,s), 6.81-6.86 (1H,m), 6.94-7.00 (3H,m), 7.32 (2H,d,J=8.0 Hz), 7.40 (2H,d,J=8.0 Hz), 7.54-7.86 (2H, m), 8.10-8.16 (2H,m), 8.29 (1H,dd,J=1.6,7.6 Hz).

Example 9

3-(3-(4-(Pyridin-2-yloxymethyl)-benzyl)-isoxazol-5-yl)-pyridin-2-yl amine dimethanesulfonate 3-(3-(4-(Pyridin-2-yloxymethyl)-benzyl)-isoxazol-5-yl)-pyridin-2-yl amine (500 mg) was dissolved in methanol (5 mL) and ethyl acetate (5 mL), and methanesulfonic acid (185 µL) was added thereto. The solvent was concentrated under a reduced pressure, to the residue were added ethanol (5 mL) and tert-butyl methyl ether (2 mL), then subjected to ultrasound treatment to be solidified. The solids were filtered to obtain the title compound (630 mg).
$^1$H-NMR Spectrum (DMSO-$d_6$) δ (ppm): 2.43 (6H,s), 4.10 (2H,s), 5.34 (2H,s), 6.90 (1H,d,J=8.4 Hz), 7.00-7.08 (3H,m), 7.34 (2H,d,J=8.0 Hz), 7.42 (2H,d,J=8.0 Hz), 7.74-7.79 (1H,m), 8.00 (2H,brs), 8.14-8.20 (2H,m), 8.38-8.42 (1H,m).

Example 10

3-(3-(4-(Pyridin-2-yloxymethyl)-benzyl)-isoxazol-5-yl)-pyridin-2-yl amine ethanesulfonate 3-(3-(4-(Pyridin-2-yloxymethyl)-benzyl)-isoxazol-5-yl)-pyridin-2-yl amine (200 mg) was dissolved in methanol (5 mL), and ethanesulfonic acid (47.8 µL) was added thereto at room temperature. This mixed solution was concentrated under a reduced pressure. To the residue thereof was added ethanol, and subjected to ultrasound treatment. Thereafter, this mixture was heated further to 60° C, and then, cooled to 0° C. To this mixed solution was added tert-butoxy methyl ether (5 mL), and subjected to ultrasound treatment. Thereafter, this mixture was heated further to 60° C, and then, cooled to 0° C. The precipitated solids were filtered, washed with a mixed solution of ethanol and tert-butoxy methyl ether (1:1), and then, in vacuo to obtain the title compound (195 mg).
$^1$H-NMR Spectrum (DMSO-$d_6$) δ (ppm): 1.04-1.08 (3H,m), 2.36-2.42 (2H,m), 4.08 (2H,s), 5.32 (2H,s), 6.86 (1H,d,J=8.4 Hz), 6.97-7.01 (3H,m), 7.34 (2H,d,J=8.0 Hz), 7.42 (2H,d,J=8.0 Hz), 7.70-7.74 (1H,m), 8.14 (1H,dd,J=5.6,2.0 Hz), 8.16-8.18 (1H,m), 8.28-8.31 (1H,m).

Example 11

3-(3-(4-(Pyridin-2-yloxymethyl)-benzyl)-isoxazol-5-yl)-pyridin-2-yl amine benzenesulfonate 3-(3-(4-(Pyridin-2-yloxymethyl)-benzyl)-isoxazol-5-yl)-pyridin-2-yl amine (100 mg) was dissolved in methanol (5 mL) and benzenesulfonic acid (46.3 mg) was added thereto. This solution was stirred at room temperature for 5 minutes, and then, concentrated in vacuo. To the residue was added ethanol (5 mL), and subjected to ultrasound treatment to cause solids to be precipitated. This solids were filtered, washed with ethanol, and then, dried under a reduced pressure to obtain the title compound (107 mg).
$^1$H-NMR Spectrum (DMSO-$d_6$) δ (ppm): 4.07 (2H,s), 5.32 (2H,s), 6.85-6.87 (1H,m), 6.91-6.94 (2H,m), 6.98-7.01 (1H,m), 7.29-7.35 (5H,m), 7.41-7.43 (2H,m), 7.58-7.61 (2H,m), 7.70-7.74 (1H,m), 8.12-8.13 (1H,m), 8.16-8.18 (1H,m), 8.20-8.21 (1H,m).

Example 12

3-(3-(4-(Pyridin-2-yloxymethyl)-benzyl)-isoxazol-5-yl)-pyridin-2-yl amine p-toluenesulfonate 3-(3-(4-(Pyridin-2-yloxymethyl)-benzyl)-isoxazol-5-yl)-pyridin-2-yl amine (100 mg) was dissolved in methanol (5 mL), and p-toluenesulfonic acid (55.7 mg) was added thereto. This mixture was stirred at room temperature for 5 minutes, and then, concentrated in vacuo. To the residue was added ethanol (5 mL), and subjected to ultrasound treatment to cause solids to be precipitated. This solids were filtered, washed with ethanol and then dried in vacuo to obtain the title compound (117 mg).
$^1$H-NMR Spectrum (DMSO-$d_6$) δ (ppm): 2.29 (3H,s), 4.07 (2H,s), 5.32 (2H,s), 6.84-6.87 (1H,m), 6.89-6.93 (2H,m), 6.98-7.01 (1H,m), 7.10-7.12 (2H,m), 7.33-7.35 (2H,m), 7.41-7.43 (2H,m), 7.46-7.48 (2H,m), 7.70-7.74 (1H,m), 8.11-8.13 (1H,m), 8.17-8.19 (2H,m).

Example 13

3-(3-(4-(Pyridin-2-yloxymethyl)-benzyl)-isoxazol-5-yl)-pyridin-2-yl amine hemifumarate 3-(3-(4-(Pyridin-2-yloxymethyl)-benzyl)-isoxazol-5-yl)-pyridin-2-yl amine (200 mg) was dissolved in methanol (2.67 mL) and ethyl acetate (2.67 mL), and fumaric acid (64.8 mg) was added thereto. The solvent was concentrated under a reduced pressure, and to the residue was added ethanol (10 mL), and dissolved by heating. Then, the solution was cooled to 0° C to be solidified. The solids were filtered to obtain the title compound (136 mg).
$^1$H-NMR Spectrum (DMSO-$d_6$) δ (ppm): 4.02 (2H,s), 5.30 (2H,s), 6.24 (2H,brs), 6.60 (1H,d,J=1.6 Hz), 6.67 (1H,dd,J=4.8,8.0 Hz), 6.78 (1H,s), 6.83 (1H,dd,J=0.8,8.0 Hz), 6.94-6.98 (1H,m), 7.30 (2H,d,J=8.0 Hz), 7.38 (2H,d,J=8.0 Hz), 7.66-7.72 (1H,m), 7.84 (1H,d,J=8.0 Hz), 8.06 (1H,d,J=4.8 Hz), 8.14 (1H,d,J=4.8 Hz).

Example 14

3-(3-(4-(Pyridin-2-yloxymethyl)-benzyl)-isoxazol-5-yl)-pyridin-2-yl amine maleate 3-(3-(4-(Pyridin-2-yloxymethyl)-benzyl)-isoxazol-5-yl)-pyridin-2-yl amine (150 mg) was dissolved in methanol (2 mL) and ethyl acetate (2 mL), and maleic acid (48.6 mg) was added thereto. The solvent was concentrated under a reduced pressure, to the residue was added ethanol (10 mL), and dissolved by heating. Then, the solution was cooled to 0° C to be solidified. The solids were filtered to obtain the title compound (136 mg).
$^1$H-NMR Spectrum (DMSO-$d_6$) δ (ppm): 4.02 (2H,s), 5.30 (2H,s), 6.22 (2H,s), 6.45 (2H,brs), 6.72 (1H,dd,J=4.8,7.6 Hz), 6.82 (1H,s), 6.83 (1H,d,J=8.4 Hz), 6.94-6.98 (1H,m), 7.31 (2H,d,J=8.0 Hz), 7.39 (2H,d,J=8.0 Hz), 7.67-7.72 (1H,m), 7.90-7.93 (1H,m), 8.07 (1H,dd,J=2.0,5.2 Hz), 8.13-8.16 (1H,m).

Example 15

3-(3-(4-(Pyridin-2-yloxymethyl)-benzyl)-isoxazol-5-yl)-pyridin-2-yl amine hemisuccinate 3-(3-(4-(Pyridin-2-yloxymethyl)-benzyl)-isoxazol-5-yl)-pyridin-2-yl amine (200 mg) was dissolved in methanol (10 mL), and succinic acid (65.8 mg) was added thereto. This reaction mixture as stirred at room temperature for 5 minutes, and then, concentrated under a reduced pressure. To the residue was added ethanol (10 mL), heated using an oil bath at 60° C, then cooled to 0° C to cause a solid to be precipitated. The solids were collected, washed with ethanol, and then, dried in vacuo to obtain the title compound (83 mg).

¹H-NMR Spectrum (DMSO-d₆) δ (ppm): 2.40 (2H,s), 4.04 (2H,s), 5.32 (2H,s), 6.26 (1H,brs), 6.69 (1H,dd,J=4.8,8.0 Hz), 6.81 (2H,s), 6.84-6.87 (1H,m), 6.97-7.00 (1H,m), 7.33 (2H, d,J=8.0 Hz), 7.41 (2H,d,J=8.0 Hz), 7.69-7.74 (1H,m), 7.87 (1H,d,J=1.6,7.2 Hz), 8.09 (1H,dd,J=1.6,4.8 Hz), 8.16-8.18 (1H,m).

Example 16

3-(3-(4-(Pyridin-2-yloxymethyl)-benzyl)-isoxazol-5-yl)-pyridin-2-yl amine citrate To 3-(3-(4-(pyridin-2-yloxymethyl)-benzyl)-isoxazol-5-yl)-pyridin-2-yl amine (1 g) and citric acid (564 mg) was added methanol (3 mL), and the suspension was stirred at 30 to 35° C, to turn it into a solution. Under stirring at 30° C, after adding tert-butyl methyl ether (3 mL) dropwise over 15 minutes to this solution and seeding, crystals precipitated. After stirring at 30° C for 10 minutes, tert-butyl methyl ether (15 mL) was added at the same temperature for one hour, and after slow cooling, mixture was stirred at 23° C for two hours. The precipitated crystals were filtered and dried to obtain the title compound (1.34 g) as a white crystal.

¹H-NMR Spectrum (DMSO-d₆) δ (ppm): 2.63 (2H,d, J=15.2 Hz), 2.74 (2H,d,J=15.2 Hz), 4.02 (2H,s), 5.30 (2H,s), 6.25 (2H,brs), 6.67 (1H,dd,J=4.8,7.6 Hz), 6.79 (1H,s), 6.81-6.86 (1H,m), 6.94-6.99 (1H,m), 7.31 (2H,d,J=8.0 Hz), 7.39 (2H,d,J=8.0 Hz), 7.67-7.73 (1H,m), 7.85 (1H,dd,J=1.6,7.6 Hz), 8.07 (1H,dd,J=2.0,4.8 Hz), 8.13-8.17 (1H,m).

Example 17

3-(3-(4-(Pyridin-2-yloxymethyl)-benzyl)-isoxazol-5-yl)-pyridin-2-yl amine citrate amorphous To 3-(3-(4-(pyridin-2-yloxymethyl)-benzyl)-isoxazol-5-yl)-pyridin-2-yl amine mono citrate (54.7 mg) was added methanol (0.25 mL). This suspension was stirred at 60° C to turn it into a solution. Under stirring at 60° C, tert-butyl methyl ether (20 mL) was added dropwise to this solution. After slow cooling, nitrogen was blown at room temperature for drying. Precipitated solids were filtered and dried to obtain the title compound as a white amorphous.

Example 18

3-(3-(4-(Pyridin-2-yloxymethyl)-benzyl)-isoxazol-5-yl)-pyridin-2-yl amine

To 3-(3-(4-(pyridin-2-yloxymethyl)-benzyl)-isoxazol-5-yl)-pyridin-2-yl amine obtained in Reference Example 1 (103.7 mg) was added 2-butanone (0.5 mL). This suspension was stirred at 60° C to turn it into a solution. Under heat-stirring at 60° C, n-heptane (1.75 mL) was added dropwise after over one minute to this solution. After stirring at 60° C for 10 minutes, this solution was slowly cooled to room temperature. The precipitated crystals were filtered and dried to obtain the title compound (68 mg) as a white crystal (TYPE II).

Example 19

3-(3-(4-(Pyridin-2-yloxymethyl)-benzyl)-isoxazol-5-yl)-pyridin-2-yl amine 3-(3-(4-(Pyridin-2-yloxymethyl)-benzyl)-isoxazol-5-yl)-pyridin-2-yl amine obtained in Reference Example 1 (67.9 g) was dissolved in ethyl acetate (700 mL), and the insoluble matter was filtered. Ethyl acetate from the filtrate was concentrated under a reduced pressure, to the residue was added tert-butyl methyl ether (100 mL), and subjected to ultrasound treatment, and then, solids were filtered. Drying was carried out at 60° C for 16 hours to obtain the title compound (60 g) as a pale yellow crystal (TYPE I).

Powder X-ray Diffraction Measurement

For each crystal and each amorphous obtained in the Examples, approximately 5 mg of the sample was ground with a mortar, then, placed on a measurement aluminum pan, and measured with the following conditions:

Apparatus used: X-ray DSC system: TTR-III (manufactured by Rigaku)
X-ray used: CuKα beam
Goniometer: TTR-III horizontal goniometer
Counter: scintillation counter
Sample plate: aluminum
Target: Cu
Tube voltage: 20 kV
Tube current: 300 mA
Scanning speed; 2.000°/min
Scanning axis: 2θ/θ
Scanning range: 2θ=2.000 to 35.000°
Divergence slit: 0.5 mm
Vertical divergence limitation slit: 2 mm
Scattering slit: open
Sensor slit: open
Sampling width: 0.02°
Integration time: 1

Figure 2:
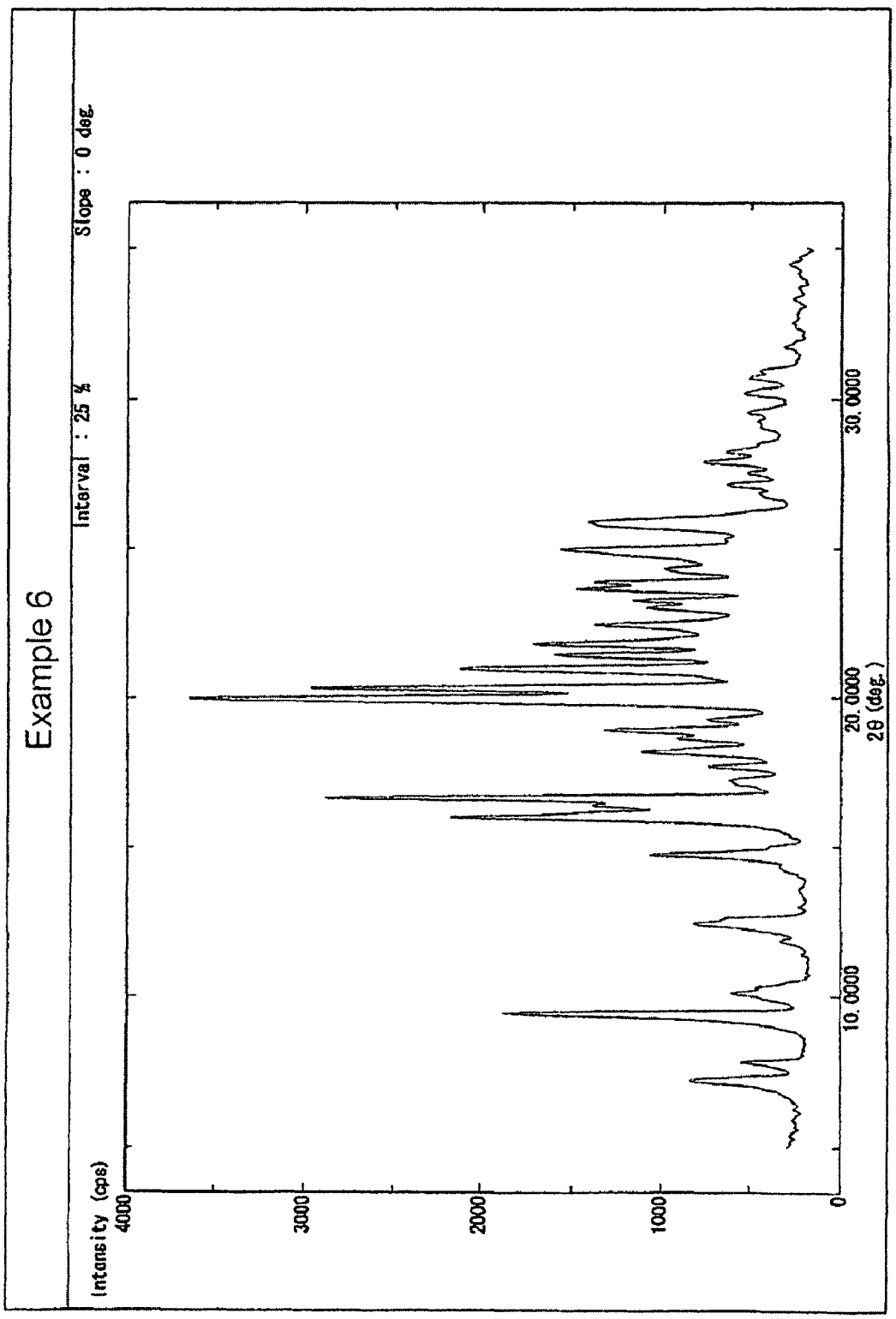
FIG. 2 shows the X-ray diffraction pattern of 3-(3-(4-(pyridin-2-yloxymethyl)-benzyl)-isoxazol-5-yl)-pyridin-2-ylamine hemisulfate anhydride obtained in Example 6 of the present invention.
Figure 3:
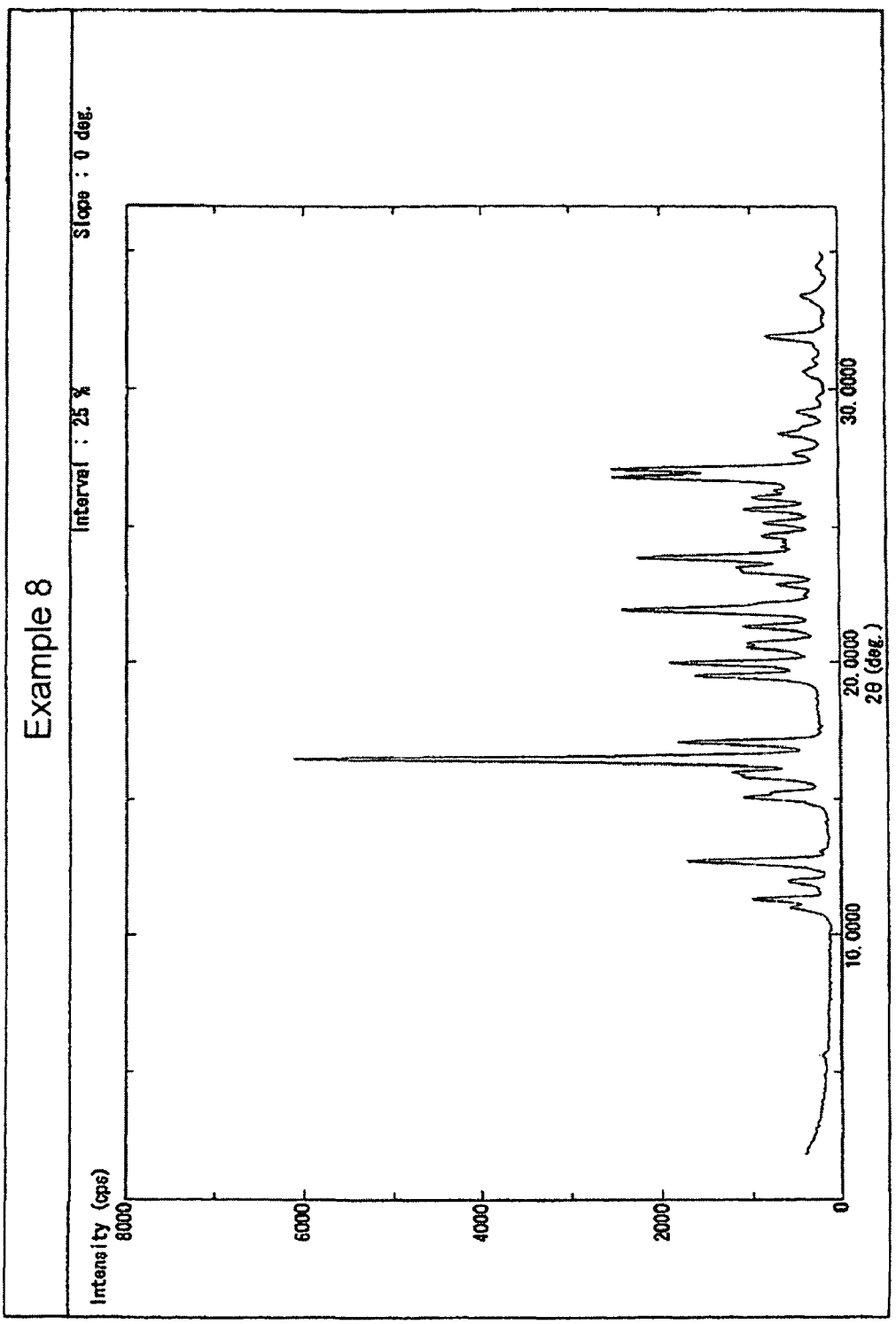
FIG. 3 shows the X-ray diffraction pattern of 3-(3-(4-(pyridin-2-yloxymethyl)-benzyl)isoxazol-5-yl)-pyridin-2-ylamine methanesulfonate anhydride obtained in Example 8 of the present invention.
Figure 4:
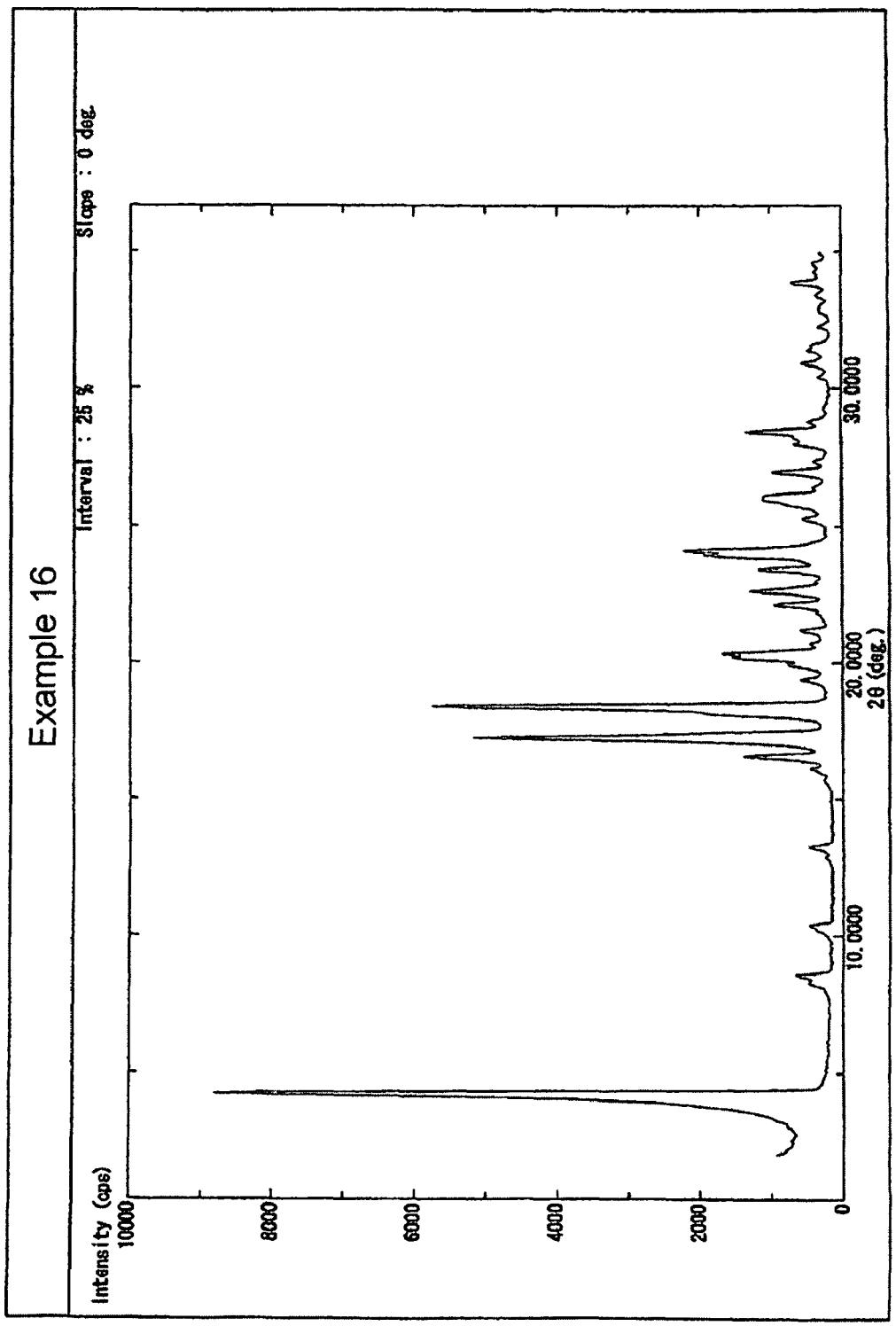
FIG. 4 shows the X-ray diffraction pattern of 3-(3-(4-(pyridin-2-yloxymethyl)-benzyl)-isoxazol-5-yl)-pyridin-2-ylamine citrate anhydride obtained in Example 16 of the present invention.
Figure 5:
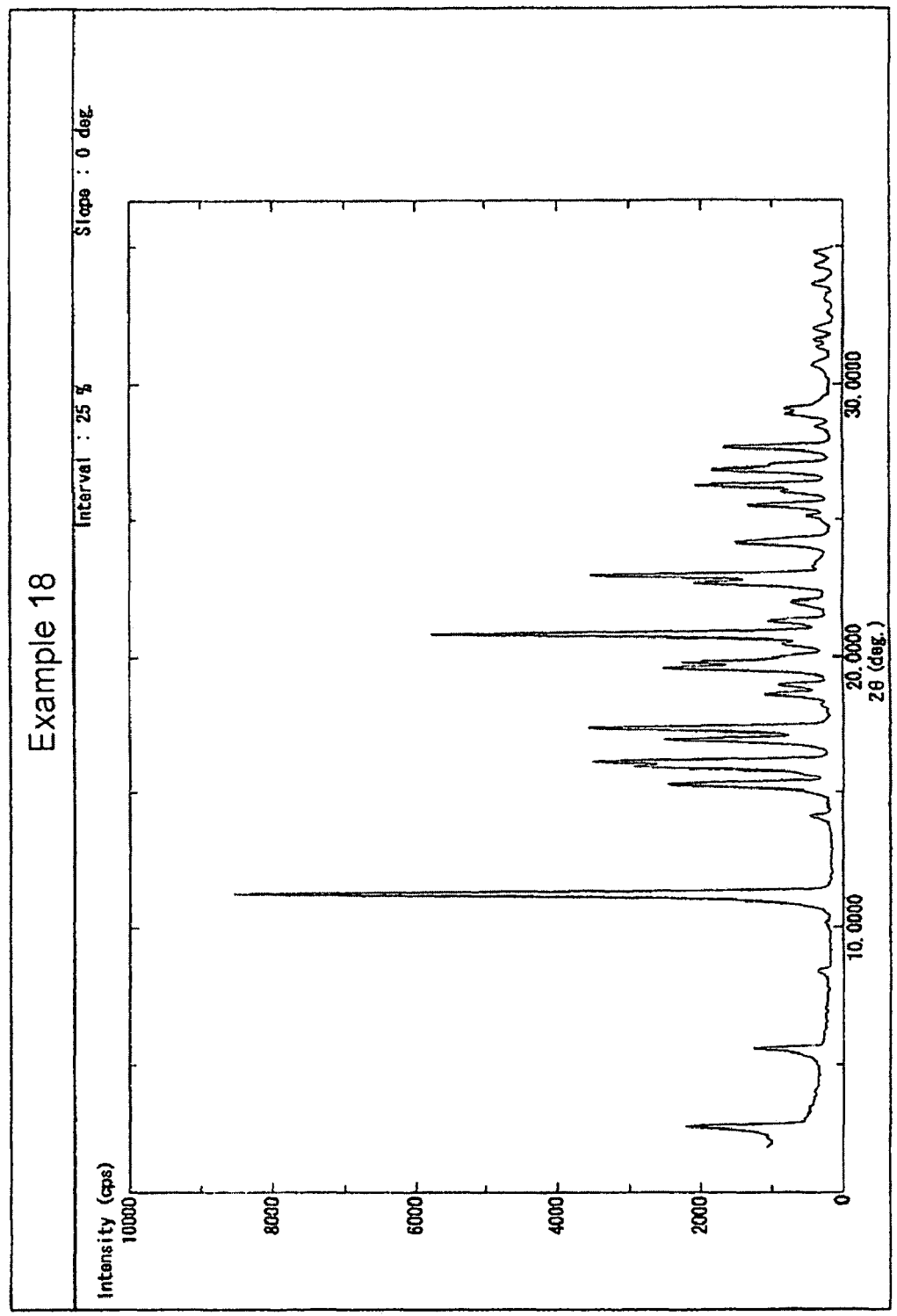
FIG. 5 shows the X-ray diffraction pattern of the free-form anhydride (TYPE II) of 3-(3-(4-(pyridin-2-yloxymethyl)-benzyl)-isoxazol-5-yl)-pyridin-2-ylamine obtained in Example 18 of the present invention.

The powder X-ray diffraction patterns for each crystal and each amorphous obtained in each of Examples are shown respectively in FIG. 1 to FIG. 6, and representative peaks and relative intensities for the diffraction angle (2θ) of each crystal described above are shown in

TABLE 1

| Example | | | | | |
|---|---|---|---|---|---|
| 1 | | 6 | | 8 | |
| Crystal | | | | | |
| Hydrochloride anhydride | | Hemisulfate anhydride | | Methanesulfonate anhydride | |
| Peak diffraction angle (2θ) | Relative intensity | Peak diffraction angle (2θ) | Relative intensity | Peak diffraction angle (2θ) | Relative intensity |
| 5.04 | 90 | 7.28 | 23 | 15.06 | 19 |
| 10.16 | 100 | 9.44 | 53 | 15.96 | 20 |
| 16.56 | 37 | 15.98 | 63 | 16.46 | 100 |
| 17.10 | 71 | 16.64 | 81 | 17.06 | 29 |
| 20.42 | 66 | 20.00 | 100 | 19.52 | 27 |
| 20.82 | 50 | 20.32 | 83 | 19.96 | 32 |
| 22.76 | 85 | 21.00 | 58 | 21.92 | 40 |
| 25.96 | 85 | 21.46 | 45 | 23.86 | 13 |
| 28.30 | 53 | 21.78 | 47 | 26.84 | 41 |
|  |  | 22.46 | 38 | 27.12 | 42 |

| Example | | | | | |
|---|---|---|---|---|---|
| 16 | | 18 | | 19 | |
| Crystal | | | | | |
| Citrate anhydride | | Free-form anhydride (TYPE II) | | Free-form anhydride (TYPE I) | |
| Peak diffraction angle (2θ) | Relative intensity | Peak diffraction angle (2θ) | Relative intensity | Peak diffraction angle (2θ) | Relative intensity |
| 4.26 | 100 | 11.26 | 100 | 6.36 | 13 |
| 8.30 | 6 | 15.28 | 30 | 9.60 | 9 |
| 8.58 | 7 | 15.90 | 34 | 16.76 | 24 |
| 1.040 | 6 | 16.12 | 40 | 18.44 | 56 |

TABLE 1-continued

| | | | | | |
|---|---|---|---|---|---|
| 17.22 | 58 | 16.94 | 30 | 18.70 | 43 |
| 18.40 | 61 | 17.36 | 44 | 19.06 | 30 |
| 20.20 | 18 | 19.58 | 30 | 19.38 | 64 |
| 23.42 | 13 | 19.80 | 27 | 20.10 | 100 |
| 23.92 | 21 | 20.82 | 66 | 20.90 | 83 |
| 24.12 | 25 | 22.94 | 42 | 21.94 | 53 |

Pharmacology Test Example

In order to demonstrate the usefulness of the acid addition salt according to the present invention, the antifungal activity of the acid addition salt according to the present invention was measured by measuring 1; activity in the experimental systemic candidal infection model in mice.

1. Experimental Systemic Candidal Infection Model in Mice (1) Preparation of Fungal Inoculant A standing culture of *C. albicans* E81022 strain was carried out for 48 hours at 30° C in sabouraud dextrose agar medium (SDA), the recovered fungal cells were suspended in sterilized physiological saline. By counting the fungal number on cytometry plate, the suspension was diluted to $2 \times 10^7$ cells/mL with sterilized physiological saline to serve fungal inoculum.

(2) Infection

The fungal inoculum was used in the amounts of 0.2 mL to inoculate 4.5 to 5.5 week-old female ICR mice in the tail vein ($4 \times 10^6$ cells/mouse).

(3) Treatment

From 0.5 and 1 hours after fungal inoculation, 0.2 mL of agent solution (compound of Reference Example 1 dissolved to 5 mg/ml in 50 mM hydrochloric acid, diluted suitably in sterile water, and then, diluted 10-fold in 5% fructose solution) was administered into the stomach using a peroral probe twice every 6 hours. The agent concentration was either 2.5 or 10 mg/kg, and the number of animals in one group was 5 animals.

(4) Determination of effects

The protective effect was determined by observing life-ldeath until 14 days after infection and calculating the mean survival days.

As a result, as shown in Table 2, mice administered with the acid addition salts according to the present invention survived for a long time as compared to the untreated group, and the compounds according to the present invention have been also found to demonstrate anti-Candida activity in vivo.

TABLE 2

| | Mean Survival Days | | |
|---|---|---|---|
| | Non-administered group | 2.5 mg/kg | 5 mg/kg |
| Hydrochloride of Reference Example 1 | 5.8 | 11.0 | 13.4 |

INDUSTRIAL APPLICABILITY

The salts or crystals of heterocycle-substituted pyridine derivatives according to the present invention 1) acts against the onset, development and persistence of infections by inhibiting fungal GPI biosynthesis, thereby inhibiting expression of cell wall proteins and blocking cell wall assembly while preventing the fungus from attaching to cells so that the pathogen cannot become pathogenic, and 2) is superior in terms of physical properties, safety and metabolic stability, and is extremely useful as a preventive or therapeutic agent for fungal infections.

We claim:

1. An acid addition salt of 3-(3-(4-(pyridin-2-yloxymethyl)- benzyl)-isoxazol-5-yl)-pyridin-2-yl amine, wherein said acid is selected from the group consisting of hydrochloric acid, hydrobromic acid, phosphoric acid, sulfuric acid, methane sulfonic acid, ethane sulfonic acid, benzene sulfonic acid, p-toluene sulfonic acid, fumaric acid, maleic acid, succinic acid and citric acid.

\* \* \* \* \*